(12) United States Patent
Yoshino

(10) Patent No.: US 8,681,208 B2
(45) Date of Patent: Mar. 25, 2014

(54) IMAGE PROCESSING DEVICE AND PROGRAM

(75) Inventor: Koichiro Yoshino, Tokyo (JP)

(73) Assignee: Olympus Corporation, Tokyo (JP)

( * ) Notice: Subject to any disclaimer, the term of this patent is extended or adjusted under 35 U.S.C. 154(b) by 361 days.

(21) Appl. No.: 13/087,779

(22) Filed: Apr. 15, 2011

(65) Prior Publication Data

US 2011/0254937 A1   Oct. 20, 2011

(30) Foreign Application Priority Data

Apr. 15, 2010  (JP) .................................. 2010-094142

(51) Int. Cl.
*A62B 1/04* (2006.01)
*A61B 1/00* (2006.01)
*G06F 19/00* (2011.01)

(52) U.S. Cl.
CPC ......... *A61B 1/00009* (2013.01); *A61B 1/00006* (2013.01); *G06F 19/3406* (2013.01)
USPC ................... 348/65; 348/61; 348/62; 348/63; 348/64; 348/68; 348/69; 348/70; 348/71; 348/72; 348/73; 348/74; 348/75; 348/76

(58) Field of Classification Search
CPC ............ A61B 1/00009; A61B 1/00006; G06F 19/3406
USPC ......................................................... 348/65
See application file for complete search history.

(56) References Cited

U.S. PATENT DOCUMENTS 5,902,230 A * 5/1999 Takahashi et al. ............ 600/109
7,658,710 B2 * 2/2010 Ueno et al. .................... 600/160
8,314,835 B2 * 11/2012 Kanzaki et al. ................ 348/75
2002/0175993 A1 * 11/2002 Ueno et al. ..................... 348/68
2003/0176768 A1 * 9/2003 Gono et al. .................... 600/109

(Continued)

FOREIGN PATENT DOCUMENTS

EP     1488026 B1 *  3/2010 ............... D01F 1/10
EP     2241244 A1 * 10/2010 ............... A61B 1/06

(Continued)

OTHER PUBLICATIONS

Japanese Office Action dated Dec. 17, 2013 from related Japanese Patent Application No. 2010-094142, together with an English language translation.

*Primary Examiner* — Andy Rao
*Assistant Examiner* — Shan Elahi
(74) *Attorney, Agent, or Firm* — Scully, Scott, Murphy & Presser, P.C.

(57) ABSTRACT

An image processing device includes a special light image acquisition section that acquires an image including an object image that includes information in a specific wavelength band as a special light image, an attention area detection section that detects an attention area based on a feature quantity of each pixel of the special light image, a disappearance determination section that determines whether or not the attention area has disappeared from a display target area based on a detection result for the attention area, the display target area being an area displayed on an output section, a guide information generation section that generates guide information about the attention area that has disappeared based on a determination result of the disappearance determination section, and an output control section that controls output of information including the guide information generated by the guide information generation section.

34 Claims, 18 Drawing Sheets

(56) References Cited

U.S. PATENT DOCUMENTS

| | | | |
|---|---|---|---|
| 2004/0215060 A1* | 10/2004 | Ueno et al. | 600/160 |
| 2007/0120976 A1* | 5/2007 | Matsumoto et al. | 348/71 |
| 2007/0173714 A1* | 7/2007 | Hirakawa | 600/407 |
| 2007/0183672 A1* | 8/2007 | Kotoda | 382/232 |
| 2007/0191677 A1* | 8/2007 | Nishimura et al. | 600/109 |
| 2007/0252893 A1* | 11/2007 | Shigemori | 348/65 |
| 2007/0282169 A1* | 12/2007 | Tsujita | 600/160 |
| 2008/0015415 A1* | 1/2008 | Obata et al. | 600/118 |
| 2008/0024599 A1* | 1/2008 | Hirakawa | 348/65 |
| 2008/0033242 A1* | 2/2008 | Tamura | 600/109 |
| 2008/0119691 A1* | 5/2008 | Yagi et al. | 600/109 |
| 2008/0281154 A1* | 11/2008 | Gono et al. | 600/109 |
| 2009/0118578 A1* | 5/2009 | Takasugi et al. | 600/109 |

FOREIGN PATENT DOCUMENTS

| | | | | |
|---|---|---|---|---|
| EP | 2499956 A1 * | 9/2012 | | A61B 1/04 |
| JP | 2003-93328 A | 4/2003 | | |
| JP | A-2006-068113 | 3/2006 | | |
| JP | A-2007-229053 | 9/2007 | | |
| WO | WO 2011113162 A1 * | 9/2011 | | G01J 3/28 |

\* cited by examiner

FIG. 2
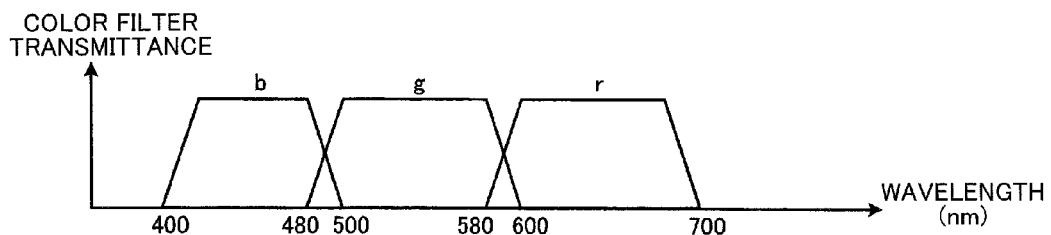
FIG. 3
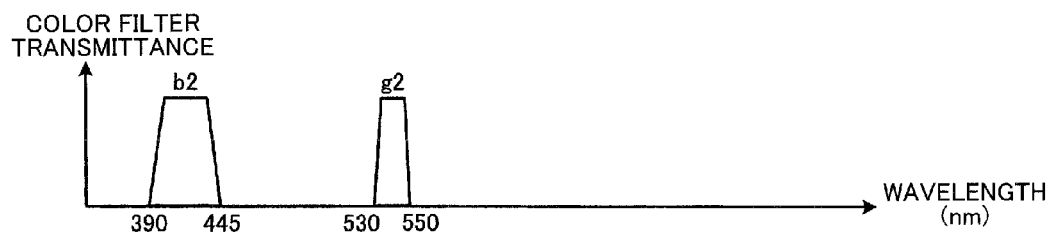
FIG. 4
| g2(0,0) | b2(1,0) | g2(2,0) | b2(3,0) | g2(4,0) | b2(5,0) |
| b2(0,1) | g2(1,1) | b2(2,1) | g2(3,1) | b2(4,1) | g2(5,1) |
| g2(0,2) | b2(1,2) | g2(2,2) | b2(3,2) | g2(4,2) | b2(5,2) |
| b2(0,3) | g2(1,3) | b2(2,3) | g2(3,3) | b2(4,3) | g2(5,3) |

| ATTENTION AREA GROUP | COORDINATES OF CENTER OF GRAVITY | AVERAGE FEATURE QUANTITY | RELIABILITY |
|---|---|---|---|
| 1 | (x1, y1) | H_ave1 | b1 |
| 2 | (x2, y2) | H_ave2 | b2 |
| 3 | (x3, y3) | H_ave3 | b3 |
| : | : | : | : |
| | | | |
| | | | |

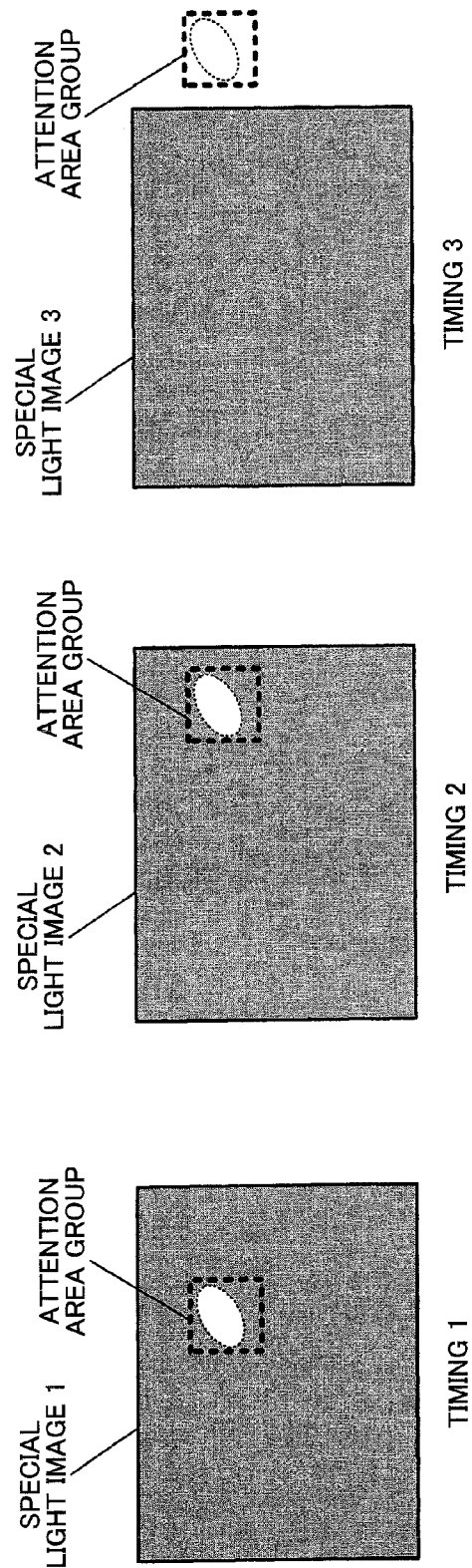

| | TIMING 1 | TIMING 2 |
|---|---|---|
| ROTARY FILTER | FILTER F1 | FILTER F2 |
| NORMAL LIGHT IMAGE STORAGE SECTION | LESION AREA / BLOOD VESSEL | NO IMAGE |
| SPECIAL LIGHT IMAGE STORAGE SECTION | NO IMAGE | [image] |

IMAGE PROCESSING DEVICE AND PROGRAM

Japanese Patent Application No. 2010-94142 filed on Apr. 15, 2010, is hereby incorporated by reference in its entirety.

BACKGROUND

The present invention relates to an image processing device, a program, and the like.

A frame sequential endoscope system that sequentially applies three colors of light (R1, G1, and B1) to tissues in a body cavity using a rotary filter, and allows diagnosis using an image (normal light image) generated from the resulting reflected light images, has been widely used. JP-A-2006-68113 discloses an endoscope system that sequentially applies narrow-band light G2 and narrow-band light B2 that differ from the above three colors of light to tissues in a body cavity, and allows diagnosis using a narrow-band light image generated from the resulting reflected light images.

JP-A-2007-229053 discloses an endoscope system that applies narrow-band excitation light to tissues in a body cavity, and allows diagnosis using a fluorescent image generated by acquiring intrinsic fluorescence or fluorescence from a fluorescent agent produced from the tissues due to the excitation light.

When using an endoscope system that acquires a narrow-band light image (e.g., JP-A-2006-68113), a lesion area (e.g., epidermoid cancer) that cannot be easily observed using normal light is visualized as a brown area differing from a normal area, so that the lesion area can be easily found.

When using an endoscope system that acquires a fluorescent image (e.g., JP-A-2007-229053), only a lesion area (e.g., tumor) produces fluorescence by utilizing a fluorescent agent that is specifically accumulated in a lesion area (e.g., tumor), so that the lesion area can be easily found.

SUMMARY

According to one aspect of the invention, there is provided an image processing device comprising:

a special light image acquisition section that acquires an image including an object image that includes information in a specific wavelength band as a special light image;

an attention area detection section that detects an attention area based on a feature quantity of each pixel of the special light image;

a disappearance determination section that determines whether or not the attention area has disappeared from a display target area based on a detection result for the attention area, the display target area being an area displayed on an output section;

a guide information generation section that generates guide information about the attention area that has disappeared based on a determination result of the disappearance determination section; and an output control section that controls output of information including the guide information generated by the guide information generation section.

According to another aspect of the invention, there is provided a program stored in an information storage medium, the program causing a computer to function as:

a special light image acquisition section that acquires an image including an object image that includes information in a specific wavelength band as a special light image;

an attention area detection section that detects an attention area based on a feature quantity of each pixel of the special light image;

a disappearance determination section that determines whether or not the attention area has disappeared from a display target area based on a detection result for the attention area, the display target area being an area displayed on an output section;

a guide information generation section that generates guide information about the attention area that has disappeared based on a determination result of the disappearance determination section; and an output control section that controls output of information including the guide information generated by the guide information generation section.

BRIEF DESCRIPTION OF THE DRAWINGS

FIG. 2 shows the RGB spectral characteristics of color filters.

FIG. 3 shows the spectral characteristics of color filters g2 and b2.

FIG. 4 is a view illustrative of color filters g2 and b2.

FIGS. 14A to 14C are views illustrative of the movement of an attention area group within a special light image at each timing.

DESCRIPTION OF EXEMPLARY EMBODIMENTS

Figure 1:
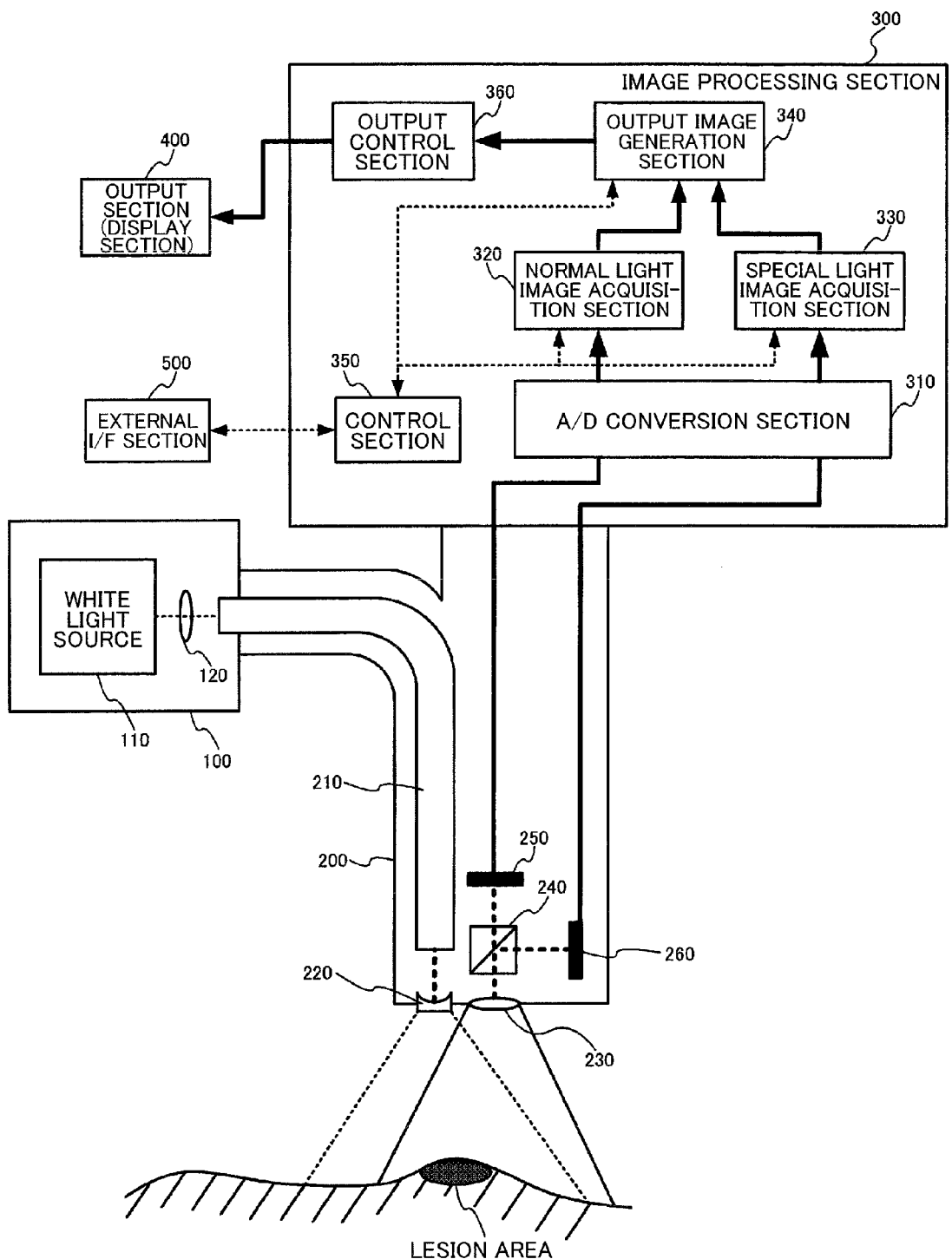
FIG. 1 shows a system configuration example according to one embodiment of the invention.

Several aspects of the invention may provide an image processing device, a program, and the like that can prevent a situation in which an attention area within a special image is missed.

Several aspects of the invention may provide an image processing device, a program, and the like that make it possible to easily found an attention area that has disappeared, and reduce the burden on a doctor by detecting an attention area within a special light image, and generating guide information based on whether or not the attention area has disappeared.

According to one embodiment of the invention, there is provided an image processing device comprising:

a special light image acquisition section that acquires an image including an object image that includes information in a specific wavelength band as a special light image;

an attention area detection section that detects an attention area based on a feature quantity of each pixel of the special light image;

a disappearance determination section that determines whether or not the attention area has disappeared from a display target area based on a detection result for the attention area, the display target area being an area displayed on an output section;

a guide information generation section that generates guide information about the attention area that has disappeared based on a determination result of the disappearance determination section; and an output control section that controls output of information including the guide information generated by the guide information generation section.

According to the above embodiment, the attention area within the special light image is detected, and whether or not the attention area has disappeared is determined. The guide information is generated based on the determination result, and the generated guide information is output. This makes it possible to easily find the attention area that has disappeared as compared with the case where the guide information is not used, so that a situation in which the attention area is missed can be prevented, for example.

According to another embodiment of the invention, there is provided a program stored in an information storage medium, the program causing a computer to function as:

a special light image acquisition section that acquires an image including an object image that includes information in a specific wavelength band as a special light image;

an attention area detection section that detects an attention area based on a feature quantity of each pixel of the special light image;

a disappearance determination section that determines whether or not the attention area has disappeared from a display target area based on a detection result for the attention area, the display target area being an area displayed on an output section;

a guide information generation section that generates guide information about the attention area that has disappeared based on a determination result of the disappearance determination section; and an output control section that controls output of information including the guide information generated by the guide information generation section.

Exemplary embodiments of the invention are described below. Note that the following embodiments do not in any way limit the scope of the invention laid out in the claims. Note also that all of the elements of the following embodiments should not necessarily be taken as essential elements of the invention.

1. First Embodiment

A method according to one embodiment of the invention is described below. A lesion area detected by observation using an endoscope may be missed when the display target area has left the lesion area. It is difficult to find the missed lesion area (attention area) again. In particular, when the doctor has not noticed that the attention area has been detected (e.g., when the doctor has concentrated on other work, or when the attention area has been detected for a very short time), the missed attention area can be found only by chance.

In order to deal with this problem, the applicant of the present application proposes the following method. As shown in FIGS. 14A to 14C, an attention area detected within a special light image moves within the image along with the movement of the imaging section of the endoscope apparatus. The display target area leaves the attention area at some timing, as shown in FIG. 14C. In this case, guide information (see FIG. 15) (an arrow in the example shown in FIG. 15) is output using the information shown in FIGS. 14A and 14B so that the missed attention area can be easily found.

A first embodiment illustrates a case where the special light image is a narrow band imaging (NBI) image. A specific example is described in section 1.1, and modifications are described in sections 1.2 to 1.4. An example in which a process according to the first embodiment is implemented by software is described in section 1.5 using a flowchart, and a detailed configuration according to the first embodiment is described in section 1.6.

A second embodiment illustrates a case where the special light image is a fluorescent image (e.g., autofluorescence imaging (AFI) image) or an infrared imaging (IRI) image.

1.1 Method

An endoscope system including an image processing device according to the first embodiment of the invention is described below with reference to FIG. 1. The endoscope system according to this embodiment includes a light source section 100, an insertion section 200, an image processing section 300, an output section 400 (display section), and an external I/F section 500.

The light source section 100 includes a white light source 110 that emits (generates) white light, and a condenser lens 120 that focuses white light on a light guide fiber 210.

The insertion section 200 is formed to be elongated and flexible (i.e., can be curved) so that the insertion section 200 can be inserted into a body cavity or the like. The insertion section 200 includes the light guide fiber 210 that guides light focused by the light source section 100, an illumination lens 220 that diffuses light that has been guided by the light guide fiber 210, and illuminates an observation target, an objective lens 230 that focuses light reflected by the observation target, a half mirror 240 that separates the focused reflected light in two, and a first imaging element 250 and a second imaging element 260 that detect the separated reflected light.

The first imaging element 250 includes a Bayer color filter array that is used to capture a normal light image. Color filters r, g, and b of the first imaging element 250 have spectral characteristics shown in FIG. 2, for example. The second imaging element 260 capture a narrow-band light image. As shown in FIG. 4, the second imaging element 260 has a configuration in which color filters g2 that allow narrow-band light G2 to pass through and color filters b2 that allow narrow-band light B2 to pass through are disposed in a staggered arrangement, for example.

As shown in FIG. 3, the color filter g2 of the second imaging element 260 allows light within a wavelength band of 530 to 550 nm to pass through, and the color filter b2 of the second imaging element 260 allows light within a wavelength band of 390 to 445 nm to pass through, for example.

The image processing section 300 includes an A/D conversion section 310, a normal light image acquisition section 320, a special light image acquisition section 330, an output image generation section 340, and a control section 350. The control section 350 is bidirectionally connected to the normal light image acquisition section 320, the special light image acquisition section 330, and the output image generation section 340, and controls the normal light image acquisition section 320, the special light image acquisition section 330, and the output image generation section 340.

The external I/F section 500 is an interface that allows the user to perform an input operation or the like on the imaging apparatus. The external I/F section 500 includes a power supply switch (power supply ON/OFF switch), a shutter button (photographing operation start button), a mode (e.g., photographing mode) switch button, and the like. The external I/F section 500 outputs input information to the control section 350.

The A/D conversion section 310 converts an analog signal output from the first imaging element 250 or the second imaging element 260 into a digital signal, and outputs the digital signal.

The normal light image acquisition section 320 acquires a normal light image from the digital signal output from the A/D conversion section 310. The special light image acquisition section 330 acquires a special light image from the digital signal output from the A/D conversion section 310. The normal light image acquisition section 320 and the special light image acquisition section 330 are described in detail later.

The normal light image acquired by the normal light image acquisition section 320 and the special light image acquired by the special light image acquisition section 330 are output to the output image generation section 340. The output image generation section 340 generates one output image from the normal light image and the special light image, and outputs the output image to the output section 400. The output image generation section 340 is described in detail later.

The normal light image acquisition section 320 is described below with reference to FIG. 5. The normal light image acquisition section 320 includes a normal light image generation section 321, and a normal light image storage section 322. When a digital signal converted by the A/D conversion section 310 has been input to the normal light image generation section 321, the normal light image generation section 321 processes the digital signal to generate a normal light image. Specifically, the normal light image generation section 321 performs an interpolation process, a white balance process, a color conversion process, a grayscale transformation process, and the like on the digital signal to generate a normal light image, and outputs the generated normal light image. The normal light image storage section 322 stores the normal light image output from the normal light image generation section 321.

The special light image acquisition section 330 is described below with reference to FIG. 6. The special light image acquisition section 330 includes a special light image generation section 331, and a special light image storage section 332. When a digital signal converted by the A/D conversion section 310 has been input to the special light image generation section 331, the special light image generation section 331 processes the digital signal to generate a special light image. In this embodiment, the special light image is a narrow-band light image.

The special light image generation section 331 generates a narrow-band light image as follows. A digital image signal input to the special light image generation section has a configuration in which the color filters g2 and b2 are disposed in a staggered arrangement (see FIG. 4). The special light image generation section 331 performs an interpolation process on the image signal to generate a G2 image in which all of the pixels have a signal value of the filter g2, and a B2 image in which all of the pixels have a signal value of the filter b2. The pixel value calculated by the interpolation process may be the average value of the four peripheral pixels. For example, the pixel value b2(1,1) at the position g2(1,1) and the pixel value g2(1,2) at the position b2(1,2) shown in FIG. 4 are calculated by the following expressions (1) and (2).

$$b2(1,1)=[b2(0,1)+b2(1,0)+b2(1,2)+b2(2,1)]/4 \quad (1)$$

$$g2(1,2)=[g2(0,2)+g2(1,1)+g2(1,3)+g2(2,2)]/4 \quad (2)$$

A color image having R, G, and B channels is generated from the G2 image and the B2 image obtained by the interpolation process. For example, a color image is generated by inputting the G2 image to the R channel of the color image, and inputting the B2 image to the G channel and the B channel of the color image.

The special light image generation section 331 performs a white balance process, a grayscale transformation process, and the like on the generated color image, and outputs the resulting color image as a narrow-band light image. The special light image storage section 332 stores the special light image output from the special light image generation section 331.

Figure 7:
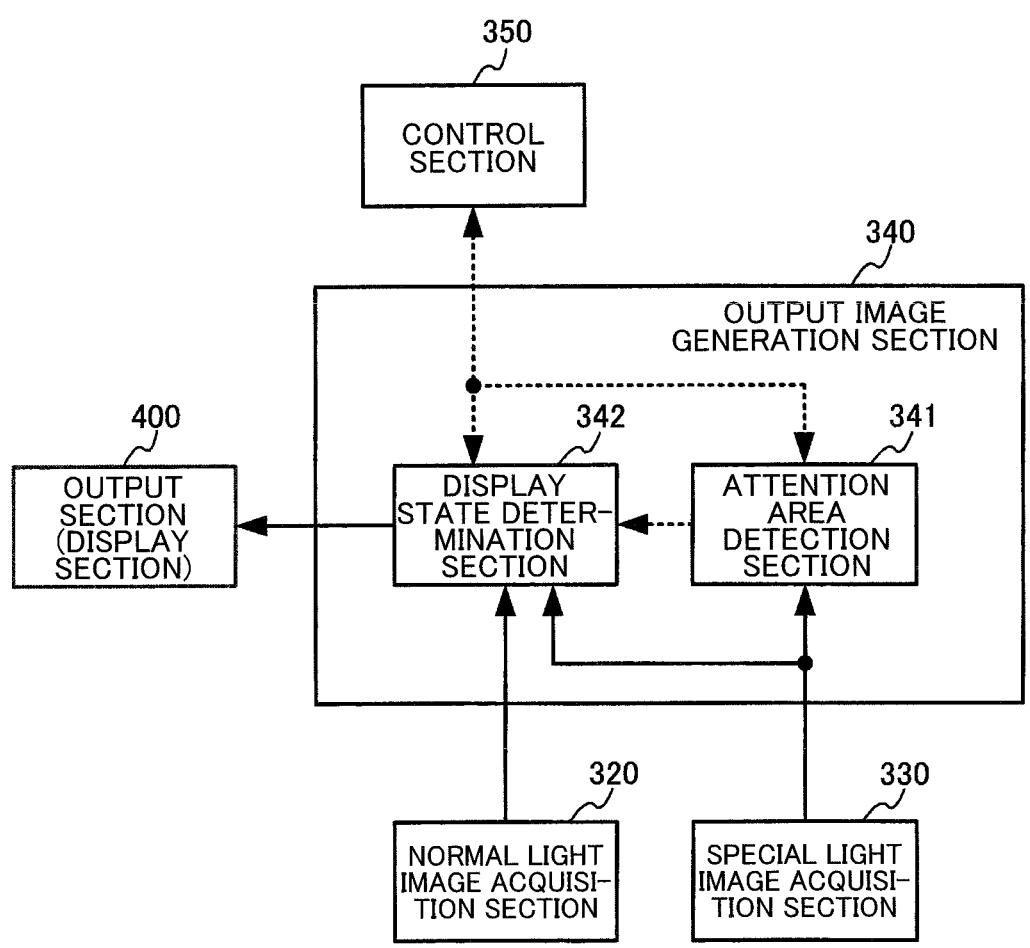
FIG. 7 shows a configuration example of an output image generation section.

A specific configuration of the output image generation section 340 is described below. FIG. 7 is a block diagram showing an example of the configuration of the output image generation section 340 according to the first embodiment. The output image generation section 340 includes an attention area detection section 341, and a display state determination section 342.

An image signal is output from the normal light image acquisition section 320 to the display state determination section 342. An image signal is output from the special light image acquisition section 330 to the attention area detection section 341 and the display state determination section 342. The attention area detection section 341 detects an attention area using the special light image output from the special light image acquisition section 330, and outputs attention area information to the display state determination section 342. The attention area detection section 341 is described in detail later. The control section 350 is bidirectionally connected to the attention area detection section 341 and the display state determination section 342, and controls the attention area detection section 341 and the display state determination section 342.

The display state determination section 342 selects the normal light image output from the normal light image acquisition section 320 or the special light image output from the special light image acquisition section 330, and outputs the selected image to the output section 400. The display state determination section 342 can process the normal light image based on the attention area information output from the attention area detection section 341, and output the processed image to the output section 400. The display state determination section 342 is described in detail later.

Figure 8:
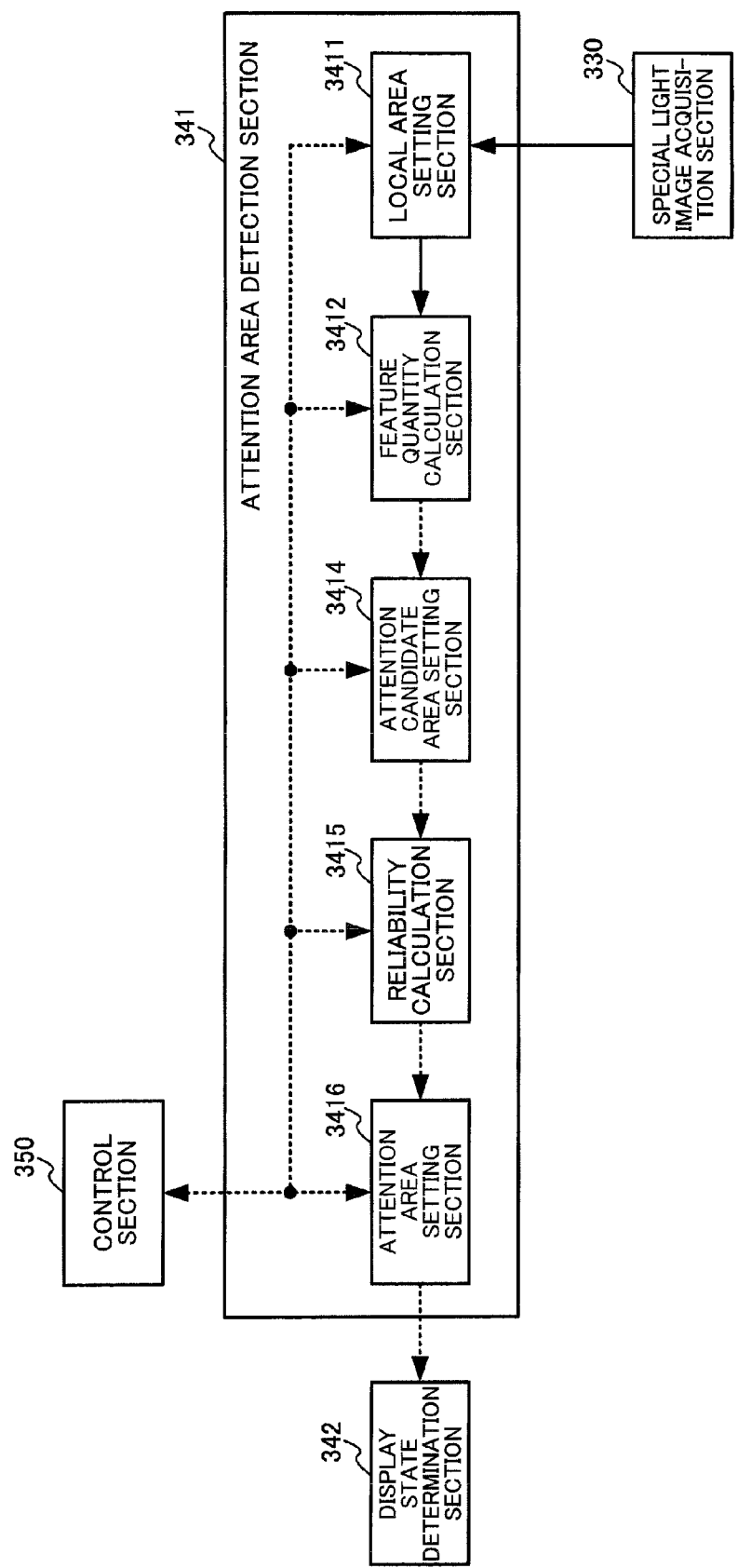
FIG. 8 shows a configuration example of an attention area detection section.

A specific configuration of the attention area detection section 341 is described below. FIG. 8 is a block diagram showing an example of the configuration of the attention area detection section 341 according to this embodiment.

The attention area detection section 341 includes a local area setting section 3411, a feature quantity calculation section 3412, an attention candidate area setting section 3414, a reliability calculation section 3415, and an attention area setting section 3416. The control section 350 is bidirectionally connected to the local area setting section 3411, the feature quantity calculation section 3412, the attention candidate area setting section 3414, the reliability calculation section 3415, and the attention area setting section 3416, and controls the local area setting section 3411, the feature quantity calculation section 3412, the attention candidate area setting section 3414, the reliability calculation section 3415, and the attention area setting section 3416.

The local area setting section 3411 sets a plurality of local areas within the special light image output from the special light image acquisition section 330. For example, the local area setting section 3411 divides the special light image into a plurality of rectangular areas, and sets each of the plurality of rectangular areas as the local areas. The size of each rectangular area may be appropriately set. In this embodiment, each local area includes 16×16 pixels (see FIG. 9). The special light image includes M×N local areas. The coordinates of each local area are indicated by (m,n). A local area at the coordinates (m,n) is indicated by a(m,n). The coordinates of the local area positioned at the upper left of the image are indicated by (0,0). The rightward direction is a positive direction (m), and the downward direction is a positive direction (n).

The local area need not necessarily be rectangular. The special light image may be divided into a plurality of arbitrary polygonal areas, and each divided area may be set as the local area. The local area may be arbitrarily set based on instructions from the user. In this embodiment, an area that includes a plurality of adjacent pixels is set as the local area in order to reduce the amount of calculations. Note that one pixel may be set as the local area. In this case, the subsequent process is performed in the same manner as in the case where each local area includes a plurality of adjacent pixels.

The feature quantity calculation section 3412 calculates a feature quantity that indicates lesion probability in each local area. In this embodiment, color information is used as an example of the feature quantity. When using a narrow-band light image as the special light image, a lesion area (e.g., epidermoid cancer) is visualized as a brown area. Therefore, the lesion area can be detected using the hue H as the feature quantity. The hue of the local area a(m,n) is indicated by H(m,n).

When calculating the hue H(m,n), the average signal value of each of the R, G, and B channels is calculated using all of the pixels included in each local area. The average signal values of the R, G, and B channels in the local area a(m,n) are respectively referred to as r, g, and b, and indicated by 8 bits (0 to 255).

The hue H(m,n) of each local area is calculated by the following expressions (3) to (8) using the average signal values r, g, and b, for example.

$$\max = \mathrm{MAX}(r,g,b) \quad (3)$$

The MAX function outputs the maximum argument among a plurality of arguments.

When max is 0:

$$H=0 \quad (4)$$

When max is not 0:

$$d = \mathrm{MAX}(r,g,b) - \mathrm{MIN}(r,g,b) \quad (5)$$

The MIN function outputs the minimum argument among a plurality of arguments.

When the average signal value r is a maximum among the average signal values r, g, and b:

$$H = 60*(g-b)/d \quad (6)$$

When the average signal value g is a maximum among the average signal values r, g, and b:

$$H = 60*\{2+(b-r)\}/d \quad (7)$$

When the average signal value b is a maximum among the average signal values r, g, and b:

$$H = 60*\{4+(r-g)\}/d \quad (8)$$

When the hue H is smaller than 0, 360 is added to the hue H. The hue H is considered to be 0 when the hue H is 360.

The attention candidate area setting section 3414 performs a threshold process on the feature quantity of each local area to detect an attention candidate area. When detecting a brown area as the attention area, a local area having a hue H of 5 to 35 may be set (detected) as the attention candidate area, for example.

The attention candidate area setting section 3414 then detects an attention candidate area group that includes adjacent attention candidate areas based on the coordinates of a plurality of local areas a(m,n) detected as the attention candidate areas, and distinguishes a plurality of attention candidate area groups by setting (adding) tag information. For example, when two attention candidate area groups have been detected (see FIG. 10), the attention candidate area setting section 3414 sets a tag value "1" to the attention candidate areas that belong to an attention candidate area group 1, and sets a tag value "2" to the attention candidate areas that belong to an attention candidate area group 2.

The attention candidate area setting section 3414 then calculates the average feature quantity of the local areas that belong to each attention candidate area group. In this embodiment, the attention candidate area setting section 3414 calculates the average hue H_ave of each attention candidate area group.

The attention candidate area setting section 3414 outputs the coordinates of each local area a(m,n) that belongs to the attention candidate area group and the average feature quantity to the reliability calculation section 3415 as attention candidate area information.

Note that the attention candidate area setting section 3414 may calculate the average luminance or intensity (saturation) of the local areas by a known method instead of the hue H (average hue H_ave), and detect the attention candidate area using the average luminance or intensity as the feature quantity. The attention candidate area setting section 3414 may calculate one feature quantity by arbitrarily combining the luminance information, the hue information, and the intensity information to detect the attention candidate area.

The reliability calculation section 3415 calculates the reliability of the attention candidate area group in order to determine whether or not the attention candidate area group is a lesion. In this embodiment, the reliability calculation section 3415 calculates the area of the attention candidate area group by calculating the number of attention candidate areas that belong to the attention candidate area group based on the tag information set to each attention candidate area, and uses the area of the attention candidate area group as the reliability.

Figure 10:
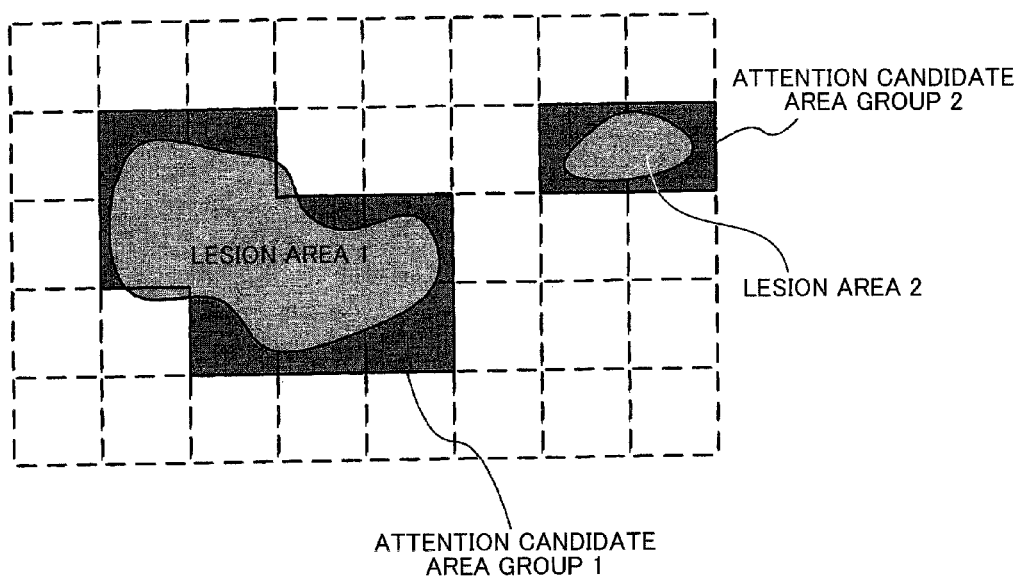
FIG. 10 is a view illustrative of an attention area group.

For example, the reliability d1 and the reliability d2 of the attention candidate area group 1 and the attention candidate area group 2 shown in FIG. 10 are respectively 9 and 2 when the area of one local area is 1. The reliability calculation section 3415 outputs the coordinates (m,n) of each local area that belongs to the attention candidate area group, the average hue H_ave, and the reliability to the attention area setting section 3416 as the attention candidate area information.

The attention area setting section 3416 sets an attention area based on the reliability included in the attention candidate area information. For example, an attention candidate area group having a reliability of 5 or more is set as the attention area. In this case, only the attention candidate area group 1 is set as the attention area. This makes it possible to exclude an attention candidate area group having a small area as noise, so that an attention area having high reliability can be detected.

The attention area setting section 3416 then calculates the coordinates (x,y) of the center of gravity of the detected attention candidate area group (hereinafter referred to as "attention area group") based on the coordinates of each local area a(m,n) that belongs to the attention area group, and outputs the coordinates (m,n) of each local area that belongs to the attention area group, the coordinates (x,y) of the center of gravity of the attention area group, the average hue H_ave, and the reliability to the display state determination section 342 as the attention area information. The attention area setting section 3416 also outputs a control signal that indicates whether or not the attention area has been detected within the special light image to the display state determination section 342.

In this embodiment, the area of the attention candidate area group is calculated based on the number of attention candidate areas that belong to the attention candidate area group, and used as the reliability. Note that the reliability may be calculated using the average hue, intensity, or luminance of the attention candidate areas that belong to the attention candidate area group. The reliability may also be calculated by combining the area of the attention candidate area group with the hue, the intensity, or the luminance of the attention candidate area group.

Figures 11, 12:
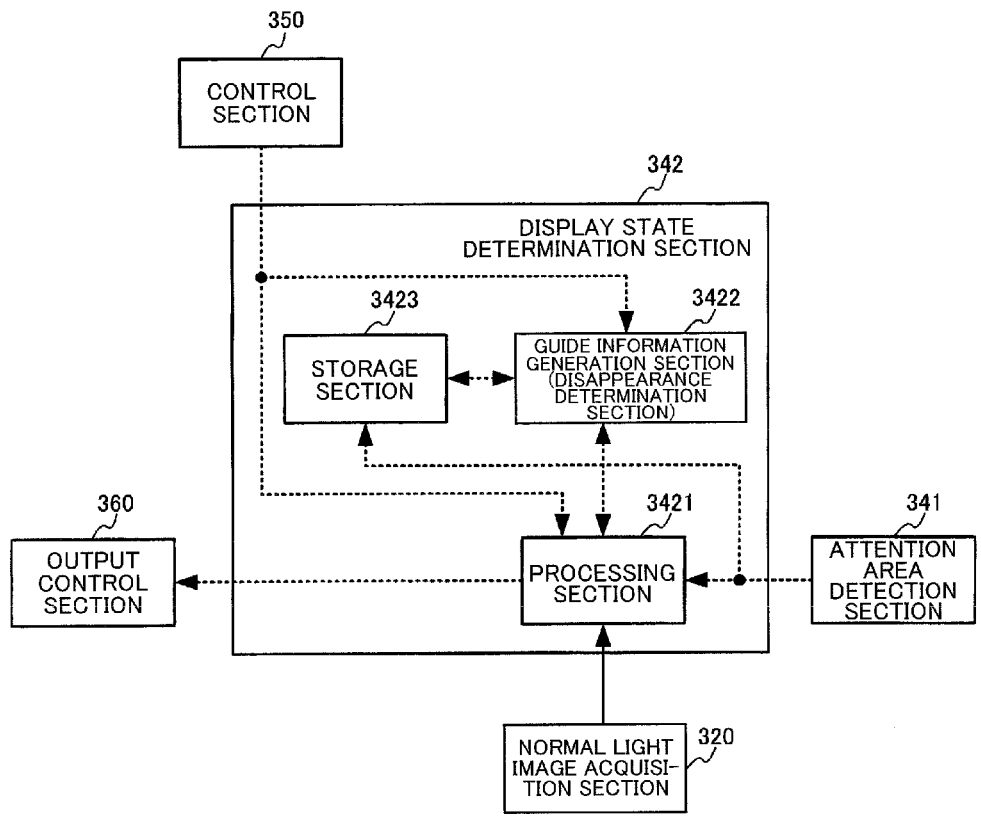
FIG. 11 shows a configuration example of a display state determination section.
FIG. 12 shows an example of attention area information stored in a storage section.

A specific configuration of the display state determination section 342 is described below. FIG. 11 is a block diagram showing an example of the configuration of the display state determination section 342 according to this embodiment. The display state determination section 342 includes a processing section 3421, a guide information generation section 3422, and a storage section 3423.

The image signals output from the normal light image acquisition section 320 and the special light image acquisition section 330 are input to the processing section 3421. The processing section 3421 processes the normal light image under control of the control section 350 using the attention area information output from the attention area detection section 341 and disappearance direction information output from the guide information generation section 3422. The processing section 3421 outputs the processed normal light image to the output section 400. The control section 350 controls the image output from the processing section 3421 to the output section 400 depending on whether or not the attention area has been detected based on instructions from the user, for example. The processing section 3421 and the guide information generation section 3422 are described in detail later.

The storage section 3423 stores the tag information that indicates the attention area group, the coordinates (x,y) of the center of gravity of the attention area group, the average feature quantity, and the reliability included in the attention area information output from the attention area detection section 341. FIG. 12 shows an example of the information stored in the storage section 3423. In FIG. 12, three attention area groups 1 to 3 are stored in the storage section 3423. This means that three attention area groups have been detected within the single-frame special light image input to the attention area detection section 341.

Note that this embodiment is applied to a motion picture, and single-frame special light images are sequentially input to the attention area detection section 341. Therefore, the attention area information detected in each frame is sequentially output from the attention area detection section 341. In this case, the storage section 3423 stores the attention area information so that the attention area information is linked to the acquisition timing of the special light image. The storage section 3423 may be a ring buffer that stores an arbitrary number of pieces of attention area information necessary for the subsequent process, for example. When the attention area has not been detected within the special light image, the storage section 3423 stores information that indicates that no attention area has been detected.

Figure 13A:
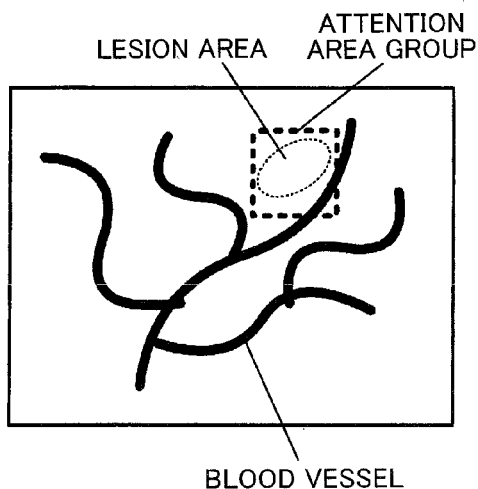
FIG. 13A shows an example of a normal light image.

A specific process performed by the processing section 3421 and the guide information generation section 3422 is described below. When the attention area detection section 341 has detected the attention area, the processing section 3421 processes the normal light image output from the normal light image acquisition section 320 using the attention area information output from the attention area detection section 341. FIG. 13A shows an example of the normal light image output from the normal light image acquisition section 320 and the attention area information output from the attention area detection section 341. Position information about all of the pixels included in the attention area group indicated by a dotted line is input to the processing section 3421 as the attention area information.

The processing section 3421 performs a color conversion process on all of the pixels included in the normal light image and input as the attention area information using the following expressions (9) to (1,1), for example. Note that r(x,y), g(x,y), and b(x,y) are R, G, and B channel signal values at the coordinates (x,y) of the normal light image before color conversion, and r_out(x,y), g_out(x,y), and b_out(x,y) are R, G, and B channel signal values of the normal light image after color conversion. T_r, T_g, and T_b are R, G, and B signal values of an arbitrary target color, and gain is an arbitrary coefficient from 0 to 1.

$$r\_out(x,y) = gain * r(x,y) + (1-gain) * T\_r \quad (9)$$

$$g\_out(x,y) = gain * g(x,y) + (1-gain) * T\_g \quad (10)$$

$$b\_out(x,y) = gain * b(x,y) + (1-gain) * T\_b \quad (1,1)$$

Figure 13B:
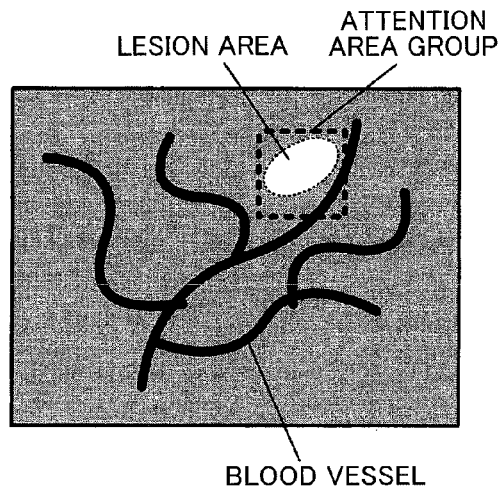
FIG. 13B shows an example of a special light image.
Figure 13C:
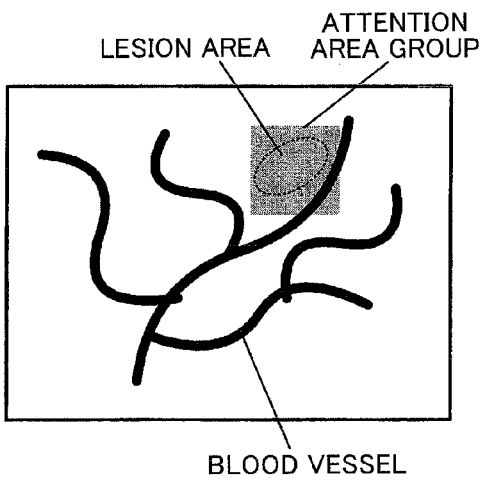
FIGS. 13C and 13D show examples of a normal light image that has been processed.

This allows the attention area group that is suspected to be a lesion area when observing the special light image shown in FIG. 13B to be superimposed on the normal light image as an area of a different color (see FIG. 13C). This makes it possible to prevent a situation in which a lesion area is missed while reducing the burden on the doctor during diagnosis using the normal light image and the special light image.

The processing section 3421 may perform the color conversion process on all of the pixels that are included in the normal light image and form the boundary of the attention area group using the following expressions (12) to (14), for example.

$$r\_out(x,y)=T\_r \quad (12)$$

$$g\_out(x,y)=T\_g \quad (13)$$

$$b\_out(x,y)=T\_b \quad (14)$$

Figure 13D:
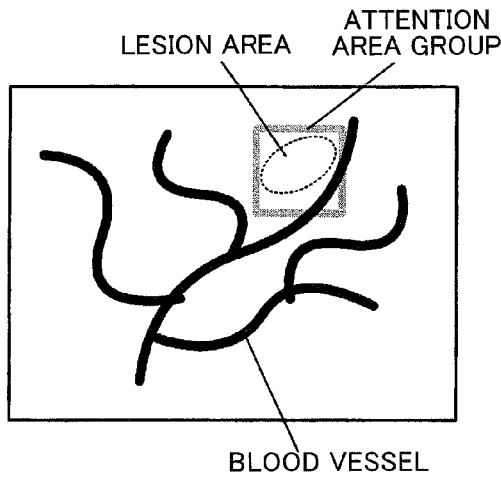

In this case, the attention area group is superimposed on the normal light image as an area enclosed by an arbitrary target color (see FIG. 13D).

FIGS. 14A to 14C are views showing a special light image output from the special light image acquisition section 330 to the attention area detection section 341 when the user moves the insertion section of the endoscope system according to this embodiment.

An attention area group has been detected within a special light image 1 acquired at a timing 1. The insertion section is moved in the leftward direction at timings 2 and 3, and the attention area group moves in the rightward direction relative to the image. As a result, the attention area group is positioned outside the image acquisition range of a special light image 3 acquired at the timing 3, so that the attention area group is not detected.

When the user has unintentionally moved the insertion section in this manner in a state in which the user does not pay attention to the image, the attention area group that is suspected to be a lesion is missed. This makes it necessary to find the attention area group again. Even if the user pays attention to the image, the attention area group is detected only for a short time when the user has quickly moved the insertion section, so that the attention area group may be missed.

In order to solve the above problems, when an attention area group has not been detected by the attention area detection section 341, the processing section 3421 outputs a control signal to the guide information generation section 3422 so that the guide information generation section 3422 estimates the disappearance direction of the attention area group. The guide information generation section 3422 estimates the disappearance direction of the attention area group based on the attention area information stored in the storage section 3423 in response to the control signal input from the processing section 3421. The following description is given on the assumption that one attention area group is detected within the special light image 1 and the special light image 2 for convenience of illustration. For example, when an attention area group has not been detected within the special light image 3 shown in FIG. 14C, the guide information generation section 3422 determines whether or not an attention area group has been detected within the special light image 1 acquired at the timing 1 shown in FIG. 14A and the special light image 2 acquired at the timing 2 shown in FIG. 14B. When an attention area group has been detected within the special light image 1 and the special light image 2, the guide information generation section 3422 calculates the motion vector V of the attention area group by the following expression (15) using the coordinates (x1_T1, y1_T1) of the center of gravity of the attention area group detected within the special light image 1 and the coordinates (x1_T2,y1_T2) of the center of gravity of the attention area group detected within the special light image 2.

$$V=(Vx,Vy)=(x1\_T2-x1\_T1,y1\_T2-y1\_T1) \quad (15)$$

The guide information generation section 3422 determines the disappearance direction of the attention area group by the following expression (16) using the calculated motion vector (Vx, Vy), for example.

Upward direction when $(Vy<0,Vx>0,|Vy|>|Vx|)$

Rightward direction when $(Vy<0,Vx>0,|Vy|<|Vx|)$

Rightward direction when $(Vy>0,Vx>0,|Vy|<|Vx|)$

Downward direction when $(Vy>0,Vx>0,|Vy|>|Vx|)$

Downward direction when $(Vy>0,Vx<0,|Vy|>|Vx|)$

Leftward direction when $(Vy>0,Vx<0,|Vy|<|Vx|)$

Leftward direction when $(Vy<0,Vx<0,|Vy|<|Vx|)$

Upward direction when $(Vy<0,Vx<0,|Vy|>|Vx|)$ (16)

Figure 15:
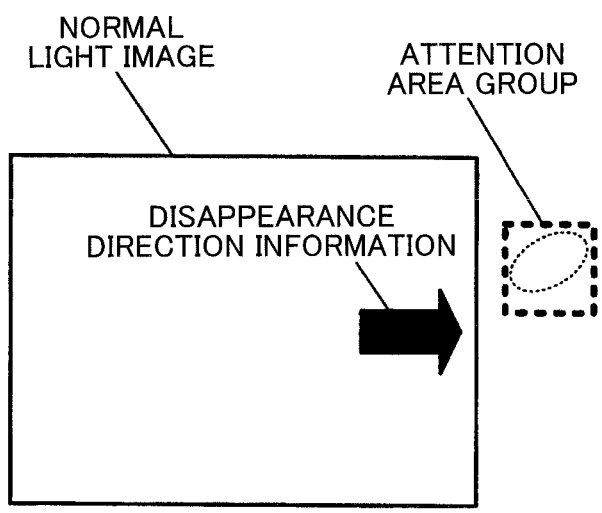
FIG. 15 shows an example of output guide information.

The guide information generation section 3422 outputs the determined disappearance direction to the processing section 3421 as disappearance direction information. The disappearance direction information is referred to as V1. In the example shown in FIG. 14, the disappearance direction information V1 indicates the rightward direction. The processing section 3421 processes the normal light image output from the normal light image acquisition section 320 using the received disappearance direction information. For example, the processing section 3421 adds the disappearance direction information V1 to the normal light image as a rightward arrow, as shown in FIG. 15.

When an attention area group has not been detected within the special light image 1 or the special light image 2, the guide information generation section 3422 does not determine the disappearance direction information. In this case, the processing section 3421 directly outputs the normal light image output from the normal light image acquisition section 320 to the output section 400.

In this embodiment, the disappearance direction information indicates one direction selected from four directions (i.e., upward direction, downward direction, leftward direction, and rightward direction). Note that the disappearance direction may be selected from eight directions including four diagonal directions, for example. In this embodiment, the disappearance direction is determined for a special light image within which an attention area has not been detected, using the attention area information detected from the special light images acquired at the preceding two timings. Note that the disappearance direction may be determined using the attention area information detected from special light images that have been acquired at arbitrary timings. In this embodiment, the disappearance direction information is added as an arrow. Note that an arbitrary symbol, character information, or the like may also be used as the disappearance direction information.

In this embodiment, when an attention area has not been detected within a special light image acquired at a timing subsequent to the timing 3, the guide information generation section 3422 determines whether or not an attention area has been detected within the special light image 2 and the special light image 3. Since an attention area group has not been detected within the special light image 3, the guide information generation section 3422 does not determine the disappearance direction information. In this case, the processing section 3421 adds the disappearance direction information V1 determined at the preceding timing to the normal light image. This also applies to a case where an attention area is not detected within a special light image acquired at the subsequent timing.

A missed attention area can be easily found by continuously adding the determined disappearance direction information to the normal light image over a given period of time. Moreover, a situation in which an attention area is missed can be prevented even if the user has quickly moved the insertion section so that the attention area has been detected only for a short time. A period in which the determined disappearance direction information is added to the normal light image may be determined based on instructions from the user via the external I/F section 500, or may be set to an arbitrary period of time in advance.

When an attention area has been detected within a newly acquired special light image, the addition of the disappearance direction information may be stopped.

Figure 16:
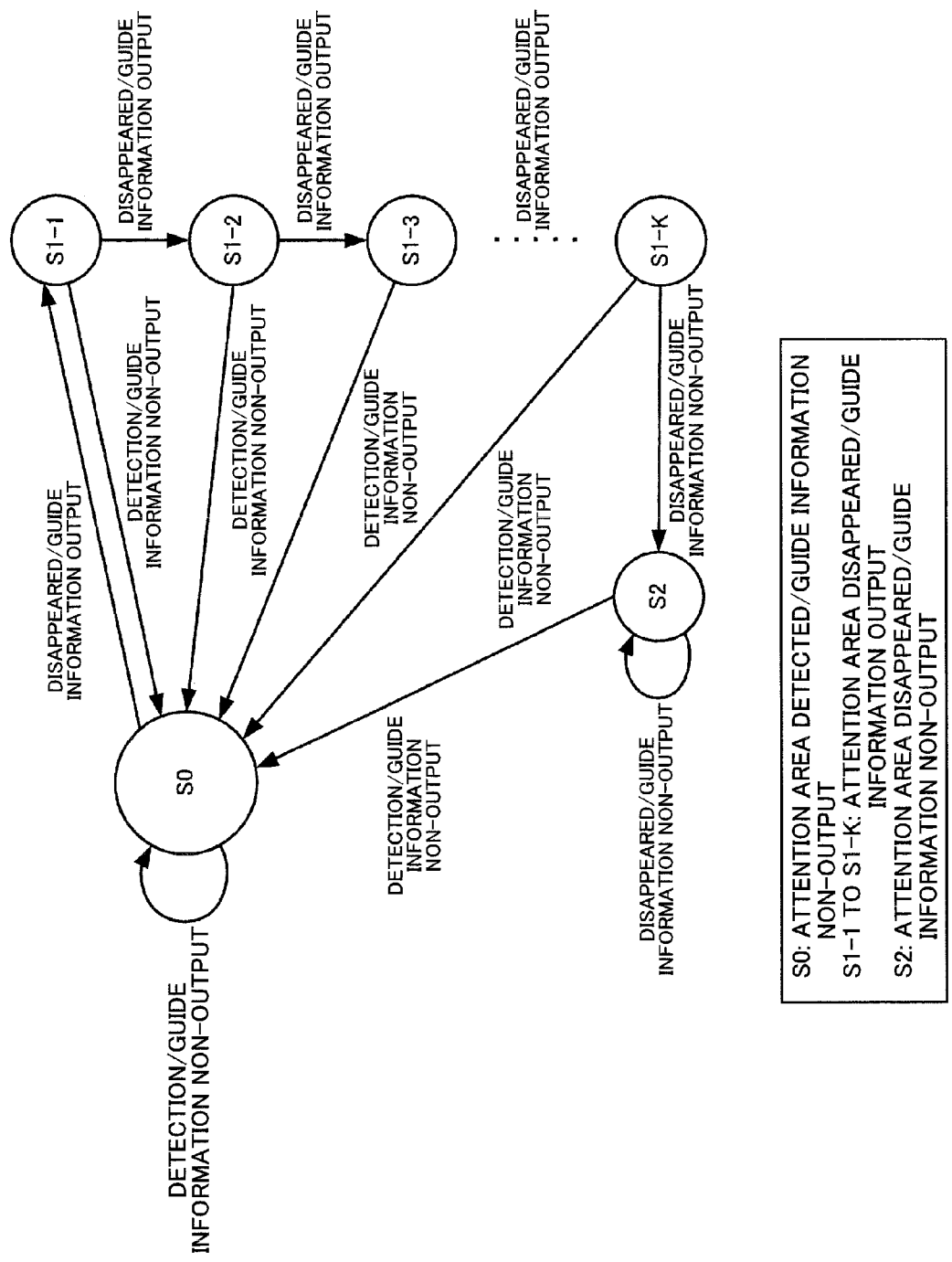
FIG. 16 is a state transition diagram illustrative of a process according to one embodiment of the invention.

The method according to this embodiment is further described below using a state transition diagram shown in FIG. 16. FIG. 16 shows an example in which identical guide information is continuously output over a given period of time. The user easily becomes aware of the guide information by outputting identical guide information over a plurality of timings (frames), so that a missed attention area can be easily found, or a situation in which an attention area is missed can be prevented.

As shown in FIG. 16, the state is roughly divided into three states (i.e., S0, S1-1 to S1-K, and S2). The state S0 refers to a state in which the attention area group has been detected (has not disappeared), and the guide information is not output. The states S1-1 to S1-K refer to a state in which the attention area group has disappeared, and the guide information is output. The state S2 refers to a state in which the attention area group has disappeared, and the guide information is not output.

Note that K is a parameter that indicates the time in which the determined disappearance direction information is continuously added to the normal light image.

The state S2 is maintained when the attention area group has disappeared. The guide information is not output in the state S2. A transition to the state S0 occurs when an attention area group has been detected. The guide information is not output in the state S0.

The state S0 is maintained when the attention area group is detected. When the attention area group has disappeared in the state S0, the guide information is output (i.e., a transition to the state S1-1 occurs). A transition to the state S1-2 occurs when the attention area group has disappeared in the state S1-1. A transition to the state S1-3 occurs when the attention area group has disappeared in the state S1-2. The guide information is output during this period.

A transition to the state S2 occurs when the attention area group has disappeared in the state S1-K, and output of the guide information is stopped. Specifically, when the guide information has been displayed, the guide information is continuously output for K frames unless the attention area group is detected.

In the example shown in FIG. 16, output of the guide information is stopped when an attention area group has been detected in the states S1-1 to S1-K, and a transition to the state S0 occurs. Specifically, when an attention area group has been detected, addition of the guide information is stopped. Note that the guide information may be continuously displayed when an attention area group has been detected.

1.2 First Modification (Addition Period Control Based on Magnitude of Motion Vector)

Modifications according to this embodiment are described below. Although an example using the direction information as the guide information has been described above, the guide information is not limited to the direction information. Since the motion vector indicates a direction and a magnitude, the output state of the guide information may be controlled based on the magnitude of the motion vector. Since the magnitude of the motion vector corresponds to information about the distance from the attention area that has disappeared group, the process can be changed depending on whether the distance from the attention area that has disappeared group is long or short, for example.

For example, the period in which the disappearance information is added to the normal light image is controlled based on the motion vector of the attention area group. Specifically, the guide information generation section 3422 calculates the magnitude V_norm of the motion vector by the following expression (17) using the motion vector V=(Vx, Vy) of the attention area group. The guide information generation section 3422 outputs the disappearance direction information and the magnitude V_norm to the processing section 3421. The processing section 3421 controls the period in which the disappearance direction information is added to the normal light image based on the magnitude V_norm.

$$V\_norm = \sqrt{Vx^2 + Vy^2} \qquad (17)$$

It is expected that the moving speed of the insertion section is high when the magnitude V_norm is large. Therefore, the accuracy of the disappearance direction information deteriorates if the disappearance direction information is added to the normal light image for a long time. Therefore, the processing section 3421 may decrease the period in which the disappearance direction information is added to the normal light image when the magnitude V_norm is large, and may increase the period in which the disappearance direction information is added to the normal light image when the magnitude V_norm is small, for example.

1.3 Modification (Example in Which a Plurality of Attention Area Groups are Detected)

An example in which one attention area group is detected within the special light image 1 and the special light image 2 has been described above for convenience of illustration. When a plurality of attention area groups have been detected, it is necessary to output the guide information in a different way. When outputting a plurality of pieces of guide information at the same time, a rightward arrow and a leftward arrow may be displayed at the same time, for example. This causes the user to be confused. In order to output only one piece of guide information, it is necessary to select the attention area group for which the guide information is output, and perform a matching process on the attention area groups within the special light image 1 and the special light image 2. In this case, the guide information generation section 3422 may perform the following process, for example.

Specifically, the guide information generation section 3422 selects an attention area group N having the highest reliability from a plurality of attention area groups detected within the special light image 2. The guide information generation section 3422 then selects an attention area group M corresponding to the attention area group N from a plurality of attention area groups detected within the special light image 1. For example, an attention area group having an average feature quantity or reliability closest to that of the attention area group N may be selected as the attention area group M.

The guide information generation section 3422 then determines the disappearance direction based on the coordinates of the center of gravity of the selected attention area groups N and M in the same manner as described above, and outputs the disappearance direction information to the processing section 3421. The processing section 3421 processes the normal light image output from the normal light image acquisition section 320 using the received disappearance direction information.

Figure 17:
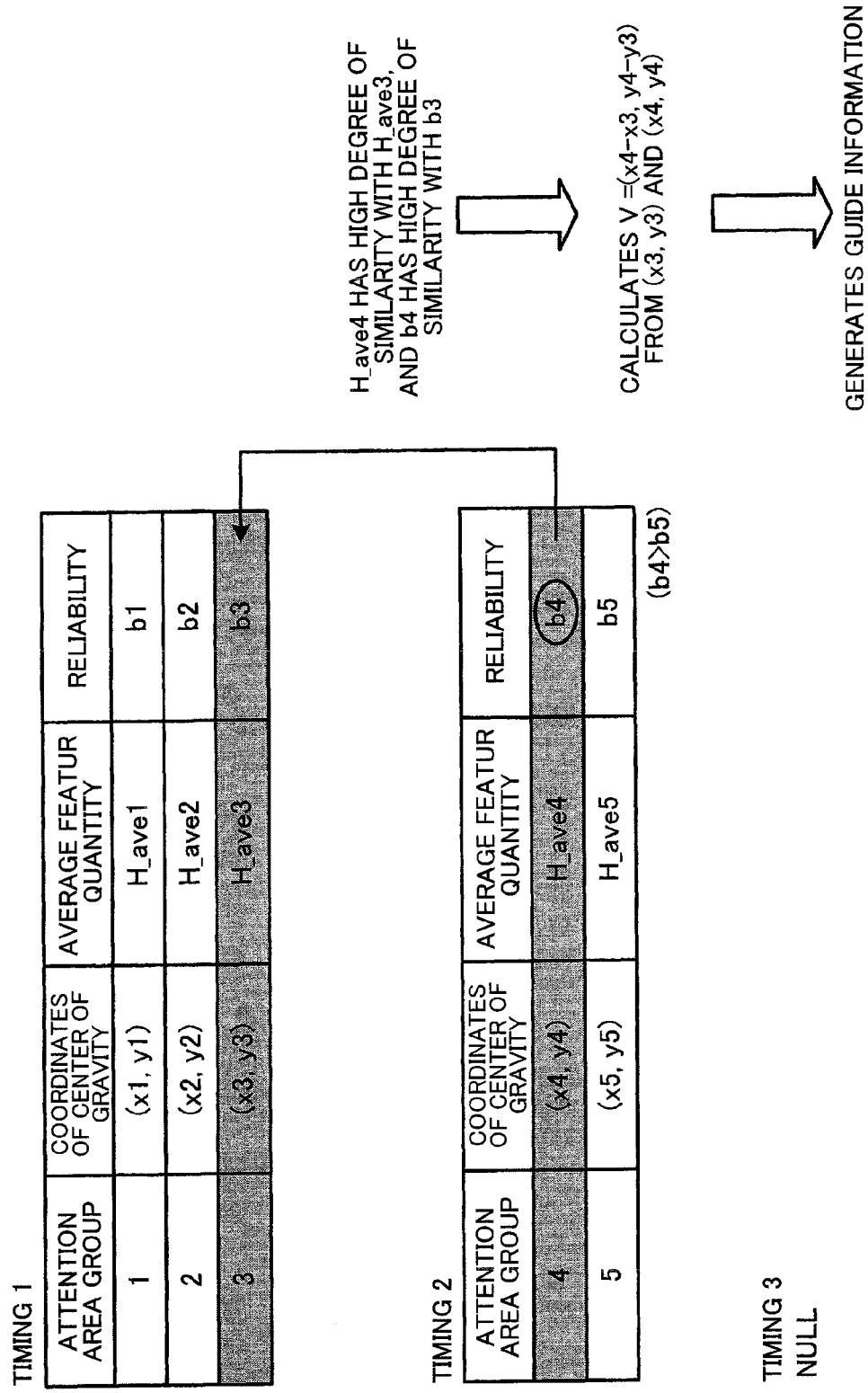
FIG. 17 is a view illustrative of a process performed when a plurality of attention area groups have been detected.

FIG. 17 shows a specific example of the above process. FIG. 17 shows an example of the structure of the attention area group data stored in the storage section 3423 in the same manner as FIG. 12. As shown in FIG. 17, three attention area groups 1 to 3 have been detected at the timing 1 (corresponding to the special light image 1), and two attention area groups 4 and 5 have been detected at the timing 2 (corresponding to the special light image 2). When an attention area group has not been detected at the timing 3 (NULL), the disappearance direction is determined based on the special light image 1 and the special light image 2.

In the example shown in FIG. 17, the attention area group detected at the timing 2 and having the reliability is selected. When b4>b5, the attention area group 4 is selected as the attention area group that corresponds to the attention area group N. The degree of similarity of the attention area groups 1 to 3 detected at the timing 1 with the attention area group 4 is calculated using at least one of the average feature quantity H_ave and the reliability b.

If the average feature quantity H_ave4 has a high degree of similarity with the average feature quantity H_ave3, and the reliability b4 has a high degree of similarity with the reliability b3, the attention area group 3 is selected as the attention area group M corresponding to the attention area group 4. The subsequent process is the same as described above. Specifically, the motion vector V is calculated from the coordinates (x4, y4) and (x3, y3), and the guide information is generated using the expression (16).

This makes it possible to display the disappearance direction of the attention area group having the highest reliability even when a plurality of attention area groups have been detected within the special light image. Moreover, a situation in which the user is confused can be prevented by displaying one disappearance direction.

1.4 Third Modification (Setting the Upper Limit of the Number of Attention Area Groups)

When a number of attention area groups are detected at the same time, a plurality of attention area groups may have a similar feature quantity or reliability. In this case, the attention area groups may not be appropriately matched. If the attention area groups are not appropriately matched, it is likely that the disappearance direction may be determined incorrectly.

In order to prevent the above problem, the guide information generation section 3422 holds information about the upper limit of the number of attention area groups. When the number of attention area groups detected within the special light image is equal to or larger than the upper limit, the guide information generation section 3422 does not determine the disappearance direction. This prevents a situation in which the disappearance direction is determined incorrectly.

1.5 Flowchart According to this Embodiment

In this embodiment, each section of the image processing section 300 is implemented by hardware. Note that the configuration of the image processing section 300 is not limited thereto. For example, a CPU may perform the process of each section on an image acquired using an imaging apparatus such as a capsule endoscope. Specifically, the process of each section may be implemented by software by causing the CPU to execute a program. Alternatively, part of the process of each section may be implemented by software.

A process performed when implementing the process of the output image generation section 340 shown in FIG. 7 on the normal light image and the special light image acquired in advance by software is described below using a flowchart shown in FIG. 18 as an example of implementing part of the process of each section by software.

Specifically, the special light image is written into the memory (Step 1), and the normal light image acquired at the same time with the special light image is written into the memory (Step 2). The attention area is detected using the special light image written into the memory, and the attention area information is output (Step 3). The display state is then determined, and a display image is output (Step 4). In this case, an image may be selected from the normal light image and the special light image written into the memory, and output as the display image. Alternatively, the normal light image or the special light image may be processed based on the attention area information output in the Step 3, and output as the display image.

The process is terminated when the process has been performed on all of the image, and the process is continuously performed when the process has not been performed on all of the image (Step 5).

Figure 18:
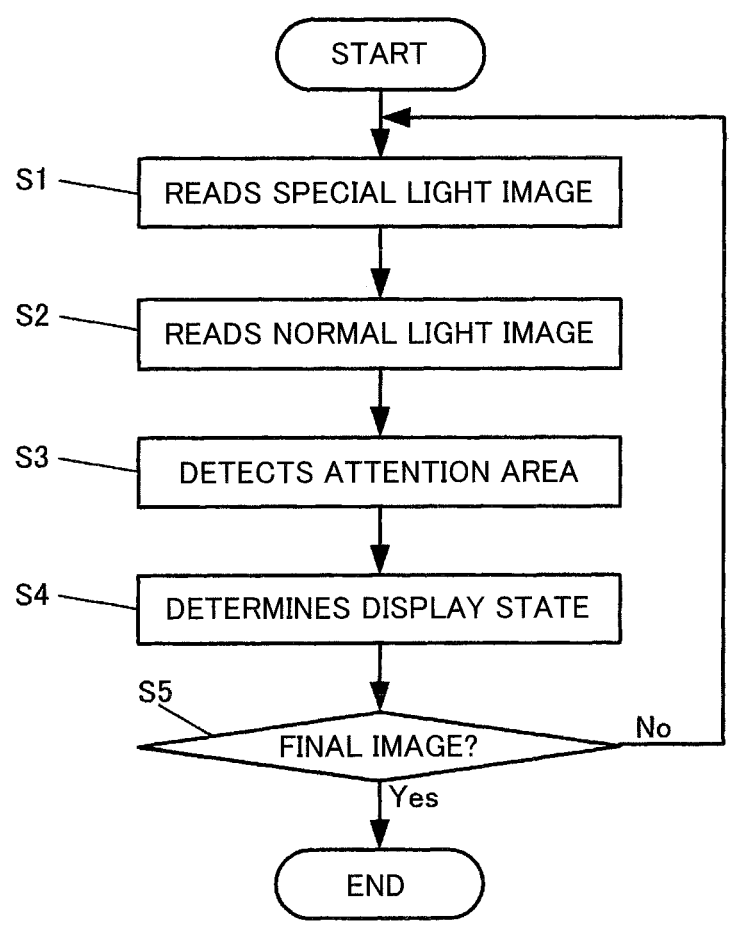
FIG. 18 is a flowchart illustrative of a process according to one embodiment of the invention.
Figure 19:
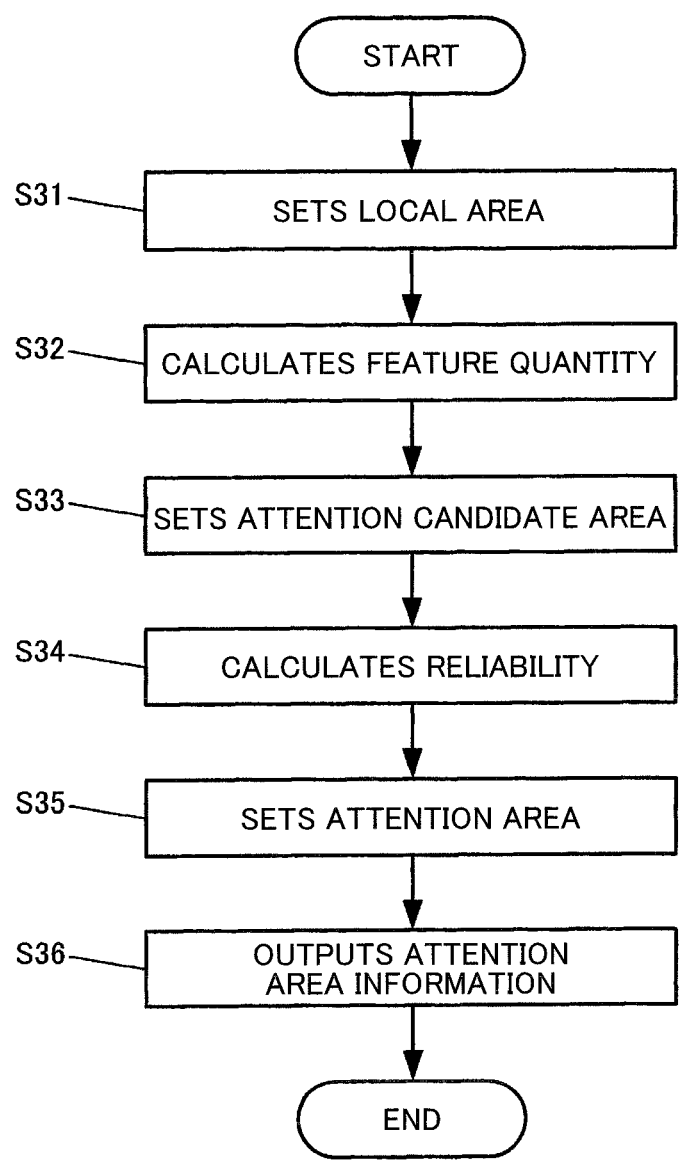
FIG. 19 is a flowchart illustrative of an attention area detection process.

A detailed process of the attention area detection step (Step 3) shown in FIG. 18 is described below using a flowchart shown in FIG. 19.

Figure 9:
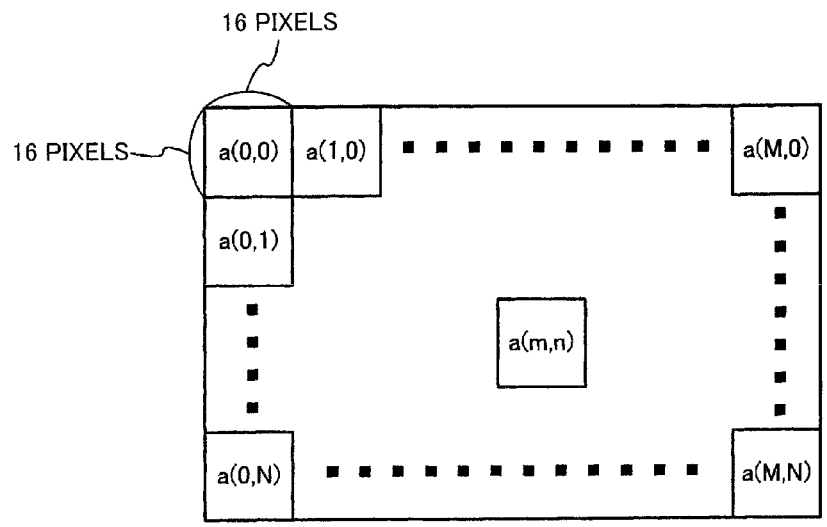
FIG. 9 is a view illustrative of a local area division method.

In a local area setting step (Step 31), a plurality of local areas are set within the special light image (see FIG. 9).

In a feature quantity calculation step (Step 32), the feature quantity of each local area is calculated. For example, the hue H indicated by the expressions (3) to (8) is used as the feature quantity.

In an attention candidate area setting step (Step 33), the threshold process is performed on the feature quantity of each local area to detect an attention candidate area. When detecting a brown area as the attention area, a local area having a hue H of 5 to 35 may be set (detected) as the attention candidate area, for example. An attention candidate area group that includes adjacent attention candidate areas is detected based on the coordinates of a plurality of local areas a(m,n) detected as the attention candidate areas, and a plurality of attention candidate area groups are distinguished by setting (adding) the tag information. The average feature quantity of the local areas that belong to each attention candidate area group is then calculated. For example, the average hue H_ave of each attention candidate area group is calculated.

In a reliability calculation step (Step 34), the reliability of the attention candidate area group is calculated in order to determine whether or not the attention candidate area group is a lesion. For example, the area of the attention candidate area group is calculated by calculating the number of attention candidate areas that belong to the attention candidate area group, and used as the reliability.

In an attention area setting step (Step 35), an attention area is set based on the reliability of the attention candidate area group. For example, an attention candidate area group having a reliability of 5 or more is set as the attention area.

In an attention area information output step (Step 36), the coordinates (x,y) of the center of gravity of the detected attention candidate area group ("attention area group") are calculated based on the coordinates of each local area a(m,n) that belongs to the attention area group, and the coordinates (m,n) of each local area that belongs to the attention area group, the coordinates (x,y) of the center of gravity of the attention area group, the average hue H_ave, and the reliability are output as the attention area information. In the attention area information output step, flag information that indicates whether or not the attention area has been detected within the special light image is also output.

Figure 20:
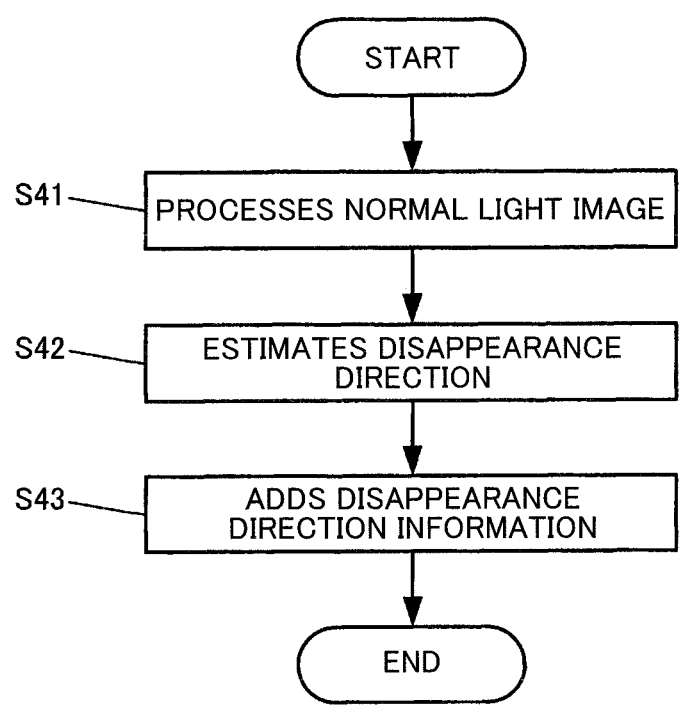
FIG. 20 is a flowchart illustrative of a display state determination process.

The process of the display state determination step (Step 4) shown in FIG. 18 is described below using a flowchart shown in FIG. 20.

In a normal light image processing step (Step 41), the normal light image is processed by the method indicated by the expressions (9) to (11) using the attention area information output in the attention area detection step.

In a disappearance direction estimation step (Step 42), the disappearance direction is estimated by the method indicated by the expressions (15) and (16) based on the flag information output in the attention area detection step.

In a disappearance direction information addition step (Step 43), the disappearance direction information estimated in the disappearance direction estimation step is added to the normal light image. For example, the determined disappearance direction information is continuously added to the normal light image for a given period.

This allows the attention area that is suspected to be a lesion area when observing the special light image shown in FIG. 13B to be superimposed on the normal light image as an area of a different color (see FIG. 13C). This makes it possible to prevent a situation in which a lesion area is missed while reducing the burden on the doctor during diagnosis using the normal light image and the special light image.

Moreover, a situation in which an attention area is missed can be prevented even if the user has quickly moved the insertion section so that the attention area has been detected only for a short time.

1.6 Detailed Configuration

According to this embodiment, the image processing device includes the special light image acquisition section 330 that acquires the special light image, as shown in FIG. 1. As shown in FIG. 7, the image processing device includes the attention area detection section 341 that detects the attention area. As shown in FIG. 11, the image processing device includes the guide information generation section (disappearance determination section) 3422. The disappearance determination section determines whether or not the attention area has disappeared from the display target area, and the guide information generation section generates the guide information about the attention area that has disappeared. As shown in FIG. 1, the image processing device includes an output control section 360 that controls output of information including the guide information.

The attention area is an area for which the observation priority is higher than that of other areas. For example, when the user is a doctor, and desires to perform treatment, the attention area refers to an area that includes a mucosal area or a lesion area. If the doctor desires to observe bubbles or feces, the attention area refers to an area that includes a bubble area or a feces area. Specifically, the attention area for the user differs depending on the objective of observation, but necessarily has an observation priority higher than that of other areas. The attention area can be detected using the feature quantity (e.g., hue or intensity) of each pixel of the second image, as described above using the expressions (3) to (8). For example, the threshold value of the feature quantity indicated by the expressions (6) to (8) changes depending on the type of attention area. For example, the threshold value of the feature quantity (e.g., hue or intensity) of a first-type attention area differs from the threshold value of the feature quantity of a second-type attention area. When the type of attention area has changed, it suffices to change the threshold value of the feature quantity, and the process (e.g., display state setting process) performed after detecting the attention area can be implemented by a process similar to the process described in connection with this embodiment.

This makes it possible to implement an image processing device that acquires the special light image, detects the attention area based on the feature quantity of each pixel of the acquired special light image, generates the guide information about the attention area that has disappeared based on the determination result for disappearance of the detected attention area, and outputs the guide information. Therefore, an image processing device that can output information as shown in FIGS. 14A to 14C and 15 can be implemented, for example. For example, the attention area (attention area group) has been detected in FIGS. 14A and 14B, and has disappeared in FIG. 14C. In this case, it is determined that the attention area has moved in the rightward direction relative to the screen based on the images shown in FIGS. 14A and 14B, and a rightward arrow is displayed as the guide information (see FIG. 15), for example. Therefore, since the guide information about the attention area that has disappeared can be output when the doctor has missed the attention area for some reason, or the attention area has been displayed only momentarily since the imaging section has been quickly moved, the attention area can be easily found again. This ensures smooth diagnosis or treatment.

The guide information generation section 3422 shown in FIG. 11 generates the direction information and the distance information as the guide information, the direction information indicating the direction from the in vivo site corresponding to the display target area (i.e., an area displayed on the display section) to the in vivo site corresponding to the attention area that has disappeared, and the distance information indicating the distance from the in vivo site corresponding to the display target area to the in vivo site corresponding to the attention area that has disappeared.

The term "in vivo site" refers to the inside of the body of the observation target. For example, when the observation target is a human, the term "in vivo site" refers to an internal site of the human body. When using an endoscope apparatus for the lower gastrointestinal tract, the term "in vivo site" refers to a large intestine or the like. The terms "display target area" and "attention area" refer to image information. It is difficult to apply the direction and the distance to the image information. Therefore, the direction information and the distance information (i.e., guide information) are defined as information that indicates the relative relationship between in vivo sites.

This makes it possible to use the direction information and the distance information as the guide information. An arrow that indicates the direction of the attention area that has disappeared or the like may be displayed as the direction information (see FIG. 15). The distance information may be calculated from FIGS. 14A and 14B. For example, when the moving distance of the attention area within the image is long, it is considered that the attention area further moves away at the next timing. In this case, the distance information may be indicated by a specific value on the assumption that the attention area makes a uniform motion or the like, or may be displayed in three stages (far, medium, or close) by performing a threshold process, for example.

The special light image acquisition section 330 acquires the first to third special light images, the attention area detection section 341 detects an attention area within each special light image, and the disappearance determination section determines whether or not the attention area has disappeared based on the attention area detection result for each special light image. When the disappearance determination section has determined that the attention area has disappeared from the third special light image, and the attention area has not disappeared from the first and second special light images, the guide information generation section 3422 generates the guide information based on the position of the attention area within the first image and the position of the attention area within the second image.

Note that the position of the attention area within the first image refers to the position of the attention area within the first special light image, and the position of the attention area within the second image refers to the position of the attention area within the second special light image. For example, the difference between the position of the attention area within the first image and the position of the attention area within the second image may be used when generating the guide information. The position of the attention area within the first image may be the center-of-gravity position of the attention area within the first special light image, and the position of the attention area within the second image may be the center-of-gravity position of the attention area within the second special light image, for example.

Therefore, when the attention area has disappeared from one special light image, but is present within two special light images differing from the special light image from which the attention area has disappeared, the guide information can be generated based on the position of the attention area within the image. FIGS. 14A to 14C show such a case. Note that FIGS. 14A to 14C (time series) may not be directly applied since the timing is not taken into consideration.

When the attention area has disappeared in FIG. 14C, the guide information is generated based on the position of the attention area within the image shown in FIG. 14A and the position of the attention area within the image shown in FIG. 14B. In FIGS. 14A and 14B, the position of the attention area within the image may be an arbitrary point within the elliptical area indicated by a dotted line, or an arbitrary point (including the center-of-gravity position of the attention area) within the square area indicated by a dotted line. The position of the attention area within the image may be an area instead of a point.

The guide information generation section 3422 calculates the motion vector of the attention area based on the difference between the position of the attention area within the first image and the position of the attention area within the second image, and generates the guide information based on the calculated motion vector.

This makes it possible to perform the process based on the motion vector as the process based on the difference in position of the attention area within the image. Since the motion vector indicates a direction and a magnitude (distance), the guide information (i.e., direction information and distance information) can be acquired in a comprehensible manner.

The output control section 360 shown in FIG. 1 may control the output time (period) of the guide information based on the motion vector. Specifically, the output control section 360 may decrease the output time (period) of the guide information when the magnitude of the motion vector is large, and may increase the output time (period) of the guide information when the magnitude of the motion vector is small. Whether the magnitude of the motion vector is large or small is determined by comparing the magnitude of the motion vector with a given threshold value.

This makes it possible to change the output time of the guide information taking account of the magnitude of the motion vector. Specifically, it is considered that the attention area moves within the image at a high speed (e.g., the imaging section of the endoscope apparatus moves or rotates at a high speed) when the magnitude of the motion vector is large, and the attention area that has disappeared has moved away to a large extent. In this case, it is difficult to find the attention area that has disappeared, and the user is confused if the guide information is displayed for a long time. Therefore, the output time of the guide information is decreased. When the magnitude of the motion vector is small, the attention area that has disappeared is positioned close to the display target area, and can be easily found. Therefore, no problem occurs even if the guide information is displayed for a long time.

The guide information generation section 3422 shown in FIG. 12 links the motion vector to one of first direction information to Nth direction information based on each coordinate component of the motion vector, and outputs the direction information linked to the motion vector as the guide information.

This makes it possible to use N directions as the direction information. Specifically, infinite directions are obtained based on the coordinate component of the motion vector. This is troublesome when outputting the guide information (e.g., displaying an arrow). It suffices to take account of only four directions (upward direction, downward direction, leftward direction, and rightward direction) by limiting N to 4 (see the expression (16)), so that the process can be facilitated. N is typically 4 or 8. Note that another number may also be used as N.

The special light image acquisition section 330 acquires a plurality of special light images respectively at a plurality of timings. The attention area detection section 341 detects an attention area within each special light image, and the disappearance determination section determines whether or not the attention area has disappeared from each special light image. The guide information is generated when the disappearance determination section has determined that the attention area has disappeared at an mth (m is an integer equal to or larger than 3) timing, and the attention area has been detected within at least two special light images at timings that precede the mth timing.

The guide information is not generated when the attention area has been detected within only one special light image or the attention area has not been detected at a timing that precedes the mth timing.

This makes it possible to generate the guide information when the guide information can be generated, and not generate the guide information when the guide information cannot be generated. The details thereof are described below with reference to FIGS. 14A to 14C. As shown in FIG. 14C, when the attention area has disappeared at some timing (m=3 in FIG. 14C), the position of the attention area at the mth timing can be estimated from the difference in position, the motion vector, or the like if the attention area has been detected within at least two special light images at timings (timings 1 and 2 in FIG. 14C) that precede the mth timing. Therefore, the guide information can be generated.

When the attention area has not been detected at the first timing, for example, only the information about the attention area detected at the second timing can be used to estimate the position of the attention area detected at the third timing. However, since the difference in position, the motion vector, or the like cannot be calculated using only one attention area, the direction and the distance cannot be estimated. In this case, a situation in which the guide information is unnecessarily output can be prevented by not generating the guide information, so that the processing load can be reduced.

The output control section 360 controls the output state of the guide information based on the determination result of the disappearance determination section. For example, when the guide information has started to be output at an Nth (N is an integer equal to or larger than 3) timing, and the attention area has continuously disappeared at the Nth to (N+K)th (K is an integer equal to or larger than 1) timings, the guide information is continuously output at the Nth to (N+K)th timings. The guide information is generated at the Nth timing.

Specifically, the guide information that has been output is continuously output for a given period (i.e., until the Kth timing is reached in the above example). If the above process is not performed, the guide information is output only at one timing (e.g., for 1/30th of a second when the frame rate is 30 frames per second). In this case, the advantages according to this embodiment (e.g., the attention area that has disappeared can be found) cannot be obtained. Therefore, the guide information is continuously output.

This corresponds to a transition between the states S1-1 and S1-K shown in FIG. 16. A transition from the state S0 to the state S1-1 corresponds to disappearance of the attention area and the start of outputting the guide information at the Nth timing. A transition from the state S1-1 to the subsequent states occurs as long as the attention area has disappeared, and the guide information is continuously output until a transition to the state S1-K occurs.

The output control section 360 may stop outputting the guide information when the attention area has been detected at a timing between the (N+1)th timing and the (N+K)th timing.

This makes it possible to stop outputting the guide information when the attention area has been detected during a period in which the guide information is output. Therefore, unnecessary guide information is not output when the attention area that has disappeared has been found, for example. This ensures smooth diagnosis or treatment by the user (doctor).

Note that an attention area differing from the attention area that has disappeared may be detected. Therefore, the guide information may be continuously output instead of stopping output of the guide information. If it is possible to determine whether or not the detected attention area is identical with the attention area that has disappeared by matching or the like, output of the guide information may be stopped when the detected attention area is identical with the attention area that has disappeared, and the guide information may be continuously output when the detected attention area differs from the attention area that has disappeared.

This corresponds to a transition from the states S1-1 and S1-K to the state S0 shown in FIG. 16. When an attention area has been detected, output of the guide information is stopped even if the output time of the guide information remains.

The output control section 360 stops output of the guide information generated at the Nth timing at the (N+K+1)th timing regardless of whether or not the attention area has disappeared.

Therefore, output of the guide information generated at the Nth timing can be stopped after the output time of the guide information has ended. It is considered that the attention area that has disappeared has moved away from the display target area if the Kth timing is reached (e.g., after K frames). It is also considered that the user does not desire to follow the attention area. In this case, it is disadvantageous to the user if the guide information is continuously output. Therefore, output of the guide information is stopped.

This corresponds to a transition from the state S1-K to the state S0 or a transition from the state S1-K to the state S2 shown in FIG. 16. The guide information is then not output regardless of whether or not the attention area has disappeared.

The output control section 360 includes a remaining output time setting section that sets remaining output time information corresponding to the output time of the guide information. The remaining output time setting section sets K as information for setting the remaining output time information.

This makes it possible to arbitrarily set the output time K of the guide information generated at the Nth timing. The remaining output time information may be a counter or the like. For example, the remaining output time information is set to K when outputting the guide information, and is decremented by one each time the guide information is output for 1 frame. When a given threshold value has been reached, output of the guide information is stopped.

The special light image acquisition section 330 acquires a plurality of special light images respectively at a plurality of timings. The attention area detection section 341 detects an attention area within each special light image, and the disappearance determination section determines whether or not the attention area has disappeared from each special light image. When the attention area has continuously disappeared at consecutive timings, the output control section 360 continuously outputs (presents) the previously generated guide information at the consecutive timings.

Therefore, when the attention area has continuously disappeared, the guide information can be continuously output at consecutive timings. The above control applies to this case when the consecutive timings correspond to the Nth to (N+K)th timings.

The image processing device includes an attention level calculation section that calculates attention level information that indicates the attention level of the attention area, and the output control section 360 controls the output state of the guide information based on the attention level information. Specifically, the output control section 360 preferentially outputs the guide information about the attention area determined to have a high attention level as compared with other attention areas based on the attention level information. The attention level information includes at least one of the feature quantity and the reliability of each pixel of the special light image, for example.

This makes it possible to set the attention level information to the attention area, and preferentially output the guide information corresponding to the attention area having a high attention level as compared with other attention areas. The attention level calculation section corresponds to the reliability calculation section 3415 shown in FIG. 8 when the attention level information is the reliability.

A specific example of the above feature is described below with reference to FIG. 17. The attention area has disappeared at the timing 3, and the guide information is generated. In this case, an attention area (attention area group 4 in FIG. 17) having the highest attention level information (reliability in FIG. 17) at the timing 2 is extracted. An attention area (attention area group 3 in FIG. 17) at the timing 1 corresponding to the extracted attention area is selected based on the similarity of the reliability and the average feature quantity. The motion vector or the like is calculated from the attention area groups 3 and 4 to generate the guide information.

Therefore, only one piece of guide information is output even if a plurality of attention areas have been detected at the same time. This makes it possible to prevent a situation in which a plurality of pieces of guide information are output at the same time (e.g., a rightward arrow and a leftward arrow are displayed at the same time).

The output control section 360 may include an upper limit setting section that sets the upper limit of the number of pieces of guide information to be output. The output control section 360 may control the output state of the guide information based on the result of comparison between the generated guide information and the upper limit set by the upper limit setting section. For example, the output control section 360 does not output the guide information when the number of pieces of generated guide information has exceeded the upper limit.

This prevents a situation in which a number of pieces of guide information are output at the same time. A number of pieces of guide information may be generated when the observation area is covered with a number of attention areas (lesion areas), for example. In this case, it is not advantageous to pay attention to each attention area. Therefore, smooth diagnosis or treatment by the doctor is ensured by preventing a situation in which a large number of pieces of guide information are output.

As shown in FIG. 1, the image processing device may include the normal light image acquisition section 320 that acquires the normal light image. The output control section 360 links the guide information to the normal light image.

This makes it possible to implement an output state shown in FIG. 15. The special light image improves the visibility of a lesion area. However, since the special light image is dark, and has a specific color, the special light image has poor visibility. Therefore, the guide information may be output so that the guide information is liked to the normal light image having high visibility.

As shown in FIG. 1, the image processing device includes the output section that outputs information including the guide information in the output state controlled by the output control section 360.

Examples of the output section include a display section. Note that the output section need not necessarily display an image. The output section may output information by outputting an alarm sound, sound, light (e.g., LED), or the like.

The term "attention area" refers to an area that indicates a lesion area.

This makes it possible to detect a lesion area as the attention area.

Specifically, the visibility of a lesion is improved using NBI, AFI, IRI, or the like to detect the lesion as the attention area.

The term "specific wavelength band" is a band that is narrower than the wavelength band of white light. Specifically, the special light image is an in vivo image, and the specific wavelength band is the wavelength band of a wavelength absorbed by hemoglobin in blood. More specifically, the specific wavelength band is 390 to 445 nm or 530 to 550 nm.

This makes it possible to observe the structure of a surface area of tissues and a blood vessel located in a deep area. A lesion area (e.g., epidermoid cancer) that cannot be easily observed using normal light can be displayed as a brown area or the like by inputting the resulting signal to a given channel (R, G, and B), so that the lesion area can be reliably detected (i.e., a situation in which the lesion area is missed can be prevented). A wavelength band of 390 to 445 nm or 530 to 550 nm is selected from the viewpoint of absorption by hemoglobin and the ability to reach a surface area or a deep area of tissues. Note that the wavelength band is not limited thereto. For example, the lower limit of the wavelength band may decrease by about 0 to 10%, and the upper limit of the wavelength band may increase by about 0 to 10% depending on a variation factor (e.g., experimental results for absorption by hemoglobin and the ability to reach a surface area or a deep area of a living body).

This embodiment also relates to a program that causes a computer to function as the special light image acquisition section 330, the attention area detection section 341, the disappearance determination section, the guide information generation section 3422, and the output control section 360. The special light image acquisition section 330 acquires the special light image, and the attention area detection section 341 detects an attention area within the special light image. The disappearance determination section determines whether or not the attention area has disappeared, and the guide information generation section 3422 generates the guide information based on the determination result of the disappearance determination section. The output control section 360 controls output of information including the guide information.

This makes it possible to store image data (e.g., capsule endoscope), and process the stored image data by software using a computer system (e.g., PC).

2. Second Embodiment

Figure 21:
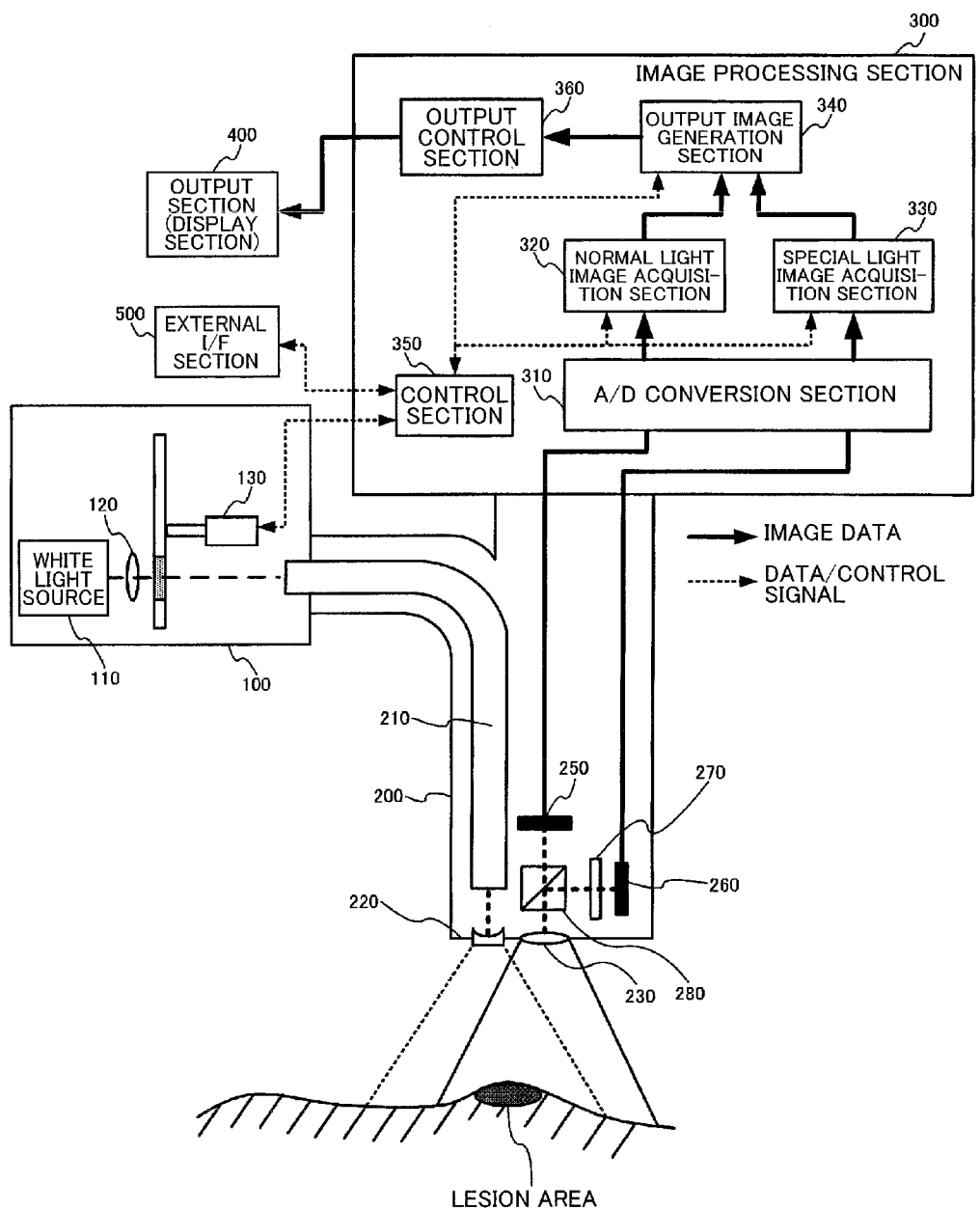
FIG. 21 shows another system configuration example according to one embodiment of the invention.

An endoscope system including an image processing device according to a second embodiment of the invention is described below with reference to FIG. 21. The endoscope system according to this embodiment includes a light source section 100, an insertion section 200, an image processing section 300, an output section 400, and an external OF section 500.

The light source section 100 includes a white light source 110 that emits (generates) white light, a condenser lens 120 that focuses light emitted from the light source on a light guide fiber 210, and a rotary filter 130 that extracts light having a specific wavelength band from white light.

Figure 22:
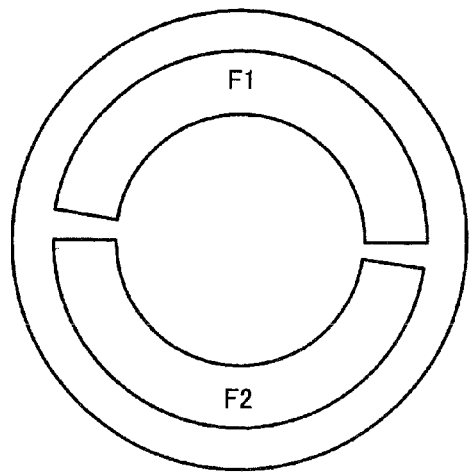
FIG. 22 shows an example of a rotary filter.
Figure 23:
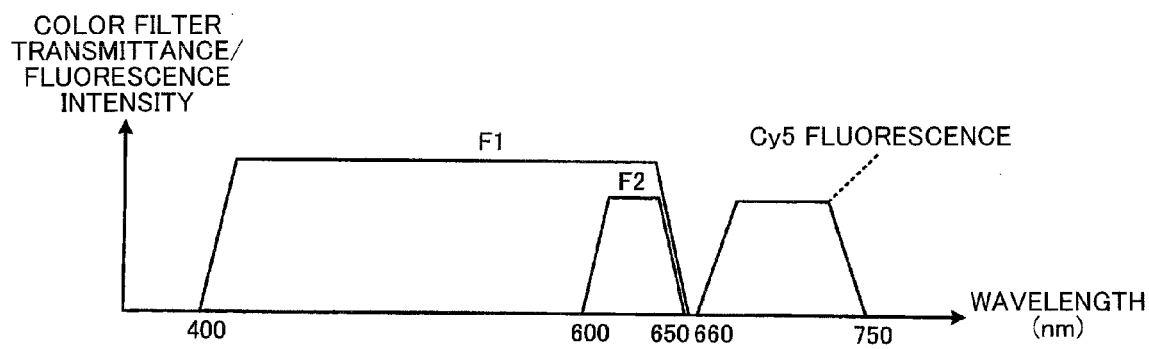
FIG. 23 shows the spectral characteristics of filters F1 and F2.

As shown in FIG. 22, the rotary filter 130 includes two color filters F1 and F2 that differ in transmittance characteristics. As shown in FIG. 22, the filter F1 allows light having a wavelength band of 400 to 650 nm to pass through, and the filter F2 allows light having a wavelength band of 600 to 650 nm to pass through, for example. The filter F1 allows white light to pass through. Light having a wavelength band of 600 to 650 nm and extracted by the filter F2 excites a fluorescent agent (e.g., Cy5) to produce fluorescence having a wavelength band of 660 to 750 nm. The fluorescent agent is specifically accumulated in a lesion area (e.g., tumor).

The insertion section 200 is formed to be elongated and flexible (i.e., can be curved) so that the insertion section 200 can be inserted into a body cavity or the like. The insertion section 200 includes the light guide fiber 210 that guides light focused by the light source section, an illumination lens 220 that diffuses light that has been guided by the light guide fiber 210, and illuminates an observation target, an objective lens 230 that focuses light reflected by the observation target, a dichroic mirror 280 that splits the focused reflected light and fluorescence into different optical paths, a barrier filter 270 that blocks excitation light included in the fluorescence split by the dichroic mirror 280, a first imaging element 250 that detects the reflected light split by the dichroic mirror 280, and a second imaging element 260 that detects the fluorescence that has passed through the barrier filter 270.

Figure 24:
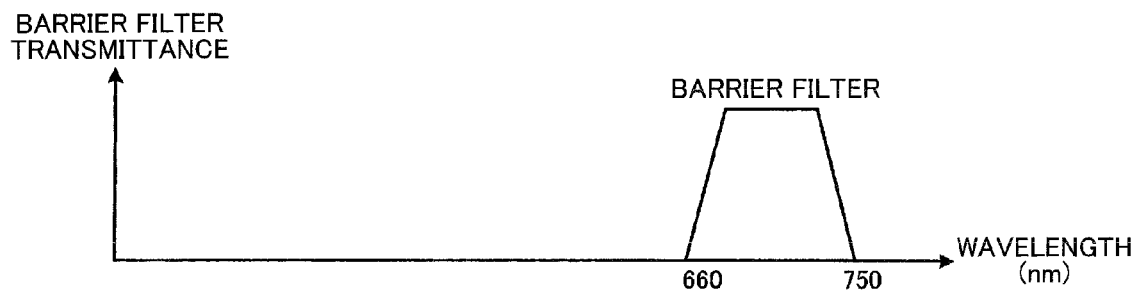
FIG. 24 shows the spectral characteristics of a barrier filter.

As shown in FIG. 24, the barrier filter 270 allows only light split from the reflected light by the dichroic mirror 280 and having a wavelength band of 660 to 750 nm (fluorescence) to pass through, and blocks the remaining light. The first imaging element 250 is a Bayer color imaging element having R, G, and B spectral characteristics shown in FIG. 2, for example. The second imaging element 260 is a monochrome imaging element that has relatively high sensitivity in a wavelength band of 660 to 750 nm, for example.

The image processing section 300 includes an A/D conversion section 310, a normal light image acquisition section 320, a special light image acquisition section 330, an output image generation section 340, and a control section 350. The control section 350 is bidirectionally connected to the normal light image acquisition section 320, the special light image acquisition section 330, and the output image generation section 340, and controls the normal light image acquisition section 320, the special light image acquisition section 330, and the output image generation section 340.

The control section 350 is also bidirectionally connected to the rotary filter 130. The rotary filter 130 causes illumination light to be applied to the observation target (i.e., tissues in a body cavity) while sequentially switching the filters F1 and F2 by driving (rotating) a motor based on a signal output from the control section 330. The control section 350 outputs information about the filters F1 and F2 disposed in an optical path to the normal light image acquisition section 320, the special light image acquisition section 330, and the output image generation section 340 as a trigger signal.

The external I/F section 500 is an interface that allows the user to input information to the endoscope system, for example.

The A/D conversion section 310 converts analog signals output from the first imaging element 250 and the second imaging element 260 into digital signals, and outputs the digital signals.

The normal light image acquisition section 320 acquires a normal light image from the digital signal output from the A/D conversion section 310. The special light image acquisition section 330 acquires a special light image from the digital signal output from the A/D conversion section 310.

The normal light image acquired by the normal light image acquisition section 320 and the special light image acquired by the special light image acquisition section 330 are output to the output image generation section 340. The output image generation section 340 generates one output image from the normal light image and the special light image, and outputs the output image to an image output section.

Figure 5:
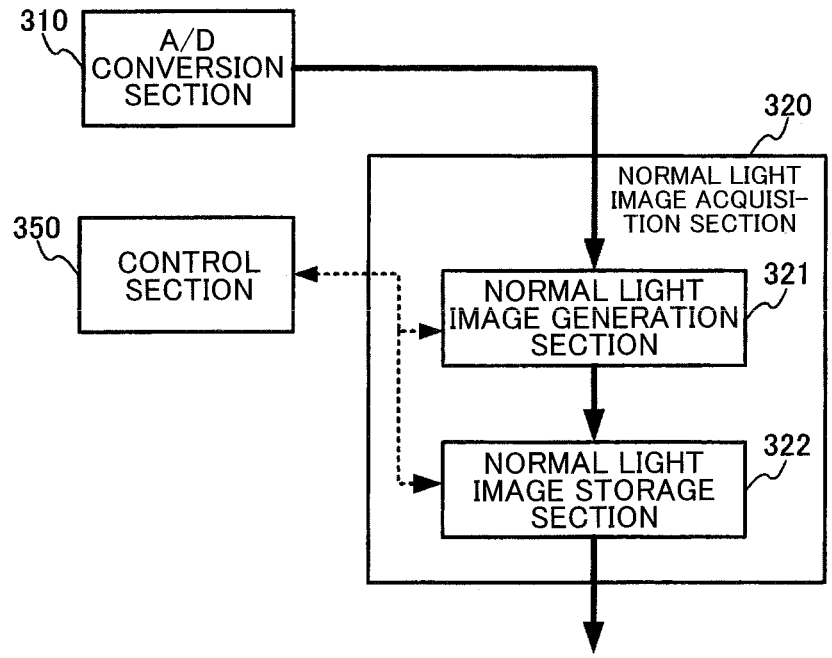
FIG. 5 shows a configuration example of a normal light image acquisition section.

As shown in FIG. 5, the normal light image acquisition section 320 includes a normal light image generation section 321, and a normal light image storage section 322. The normal light image generation section 321 identifies a period in which the filter F1 is positioned within the optical path based on the trigger signal transmitted from the control section 350, and processes a digital signal converted from an analog signal transmitted from the first imaging element in a period in which the filter F1 is positioned within the optical path to generate a normal light image. Specifically, the normal light image generation section 321 performs an interpolation process, a white balance process, a color conversion process, a grayscale transformation process, and the like on the digital signal to generate a normal light image, and outputs the normal light image. The normal light image storage section 322 stores the normal light image output from the normal light image generation section 321.

Figure 6:
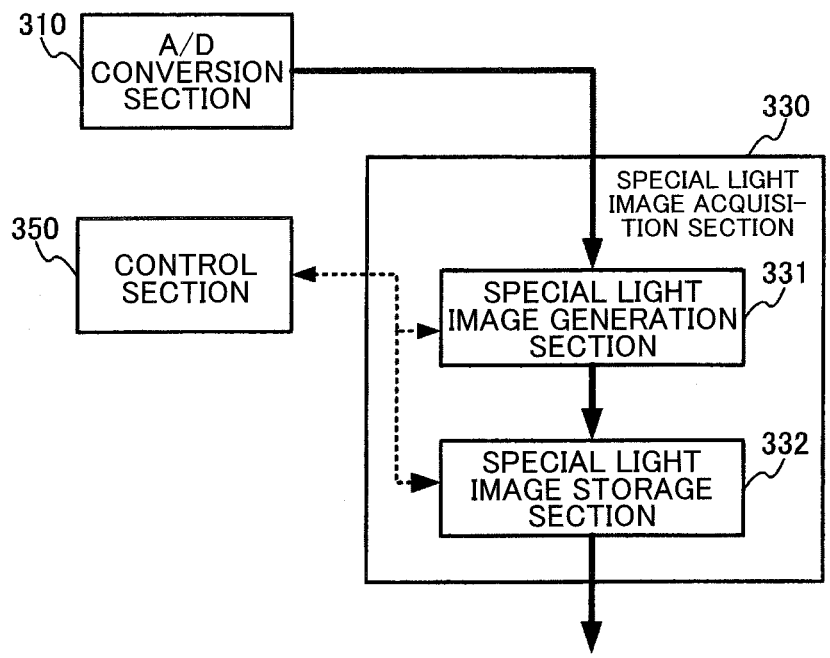
FIG. 6 shows a configuration example of a special light image acquisition section.

As shown in FIG. 6, the special light image acquisition section 330 includes a special light image generation section 331, and a special light image storage section 332. The special light image generation section 331 identifies a period in which the filter F2 is positioned within the optical path based on the trigger signal transmitted from the control section 350, and processes a digital signal converted from an analog signal transmitted from the second imaging element in a period in which the filter F2 is positioned within the optical path to generate a special light image. In this embodiment, the special light image is a monochrome fluorescent image. Specifically, the special light image generation section 331 performs an interpolation process, a gain control process, a grayscale transformation process, and the like on the image signal that indicates fluorescence produced from a lesion area where a fluorescent agent is accumulated to generate a monochrome special light image, and outputs the special light image. The special light image storage section 332 stores the special light image output from the special light image generation section 331.

Figures 25, 26:
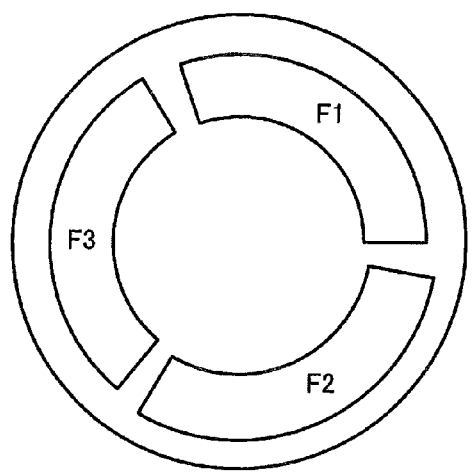
FIG. 25 shows an example of the combination of a filter and the resulting image at each timing.
FIG. 26 shows another example of a rotary filter.

FIG. 25 is a view showing the type of filter positioned within the optical path, and images stored in the normal light image storage section 322 and the special light image storage section 332. Specifically, the filter F1 is inserted into the optical path at a timing 1. In this case, white light is emitted as the illumination light. The normal light image is stored in the normal light image storage section 322 as a color image, and an image is not stored in the special light image storage section 332. The filter F2 is inserted into the optical path at a timing 2. In this case, excitation light is emitted as the illumination light. Fluorescence produced from a lesion area where a fluorescent agent is accumulated is stored in the special light image storage section 332 as a monochrome image, and an image is not stored in the normal light image storage section 322. The normal light image storage section 322 and the special light image storage section 332 can store a plurality of images.

The configuration of the output image generation section 340 is the same as in the first embodiment. In this embodiment, since the special light image is a monochrome fluorescent image, the luminance of the fluorescent image may be used as the feature quantity utilized by the attention area detection section 341, for example.

Although this embodiment utilizes two types of illumination light, three or more types of illumination light may also be used. For example, a rotary filter shown in FIG. 26 may be used. A filter F1 allows white light to pass through, a filter F2 allows first excitation light due to a fluorescent agent such as Cy5 to pass through, and a filter F3 allows second excitation light due to another fluorescent agent to pass through. In this case, the special light image can be generated by performing a pseudo-color process on a fluorescent image acquired by the second imaging element when the first excitation light is emitted and a fluorescent image acquired by the second imaging element when the second excitation light is emitted, for example. The feature quantity utilized by the attention area detection section 341 may be the hue H in the same manner as in the first embodiment, or may be luminance/color information other than the hue H. In this case, it is necessary to use a barrier filter that blocks the first excitation light and the second excitation light, but allows fluorescence due to the first excitation light and the second excitation light to pass through.

Although this embodiment utilizes a fluorescent agent, intrinsic fluorescence produced from collagen in tissues may be observed (e.g., autofluorescence imaging (AFI)), for example. In this case, light having a wavelength band of 390 to 470 nm may be used as excitation light, and a barrier filter that allows light having a wavelength band of 490 to 625 nm to pass through may be used. Light having a wavelength band of 540 to 560 nm and absorbed by hemoglobin in blood may be used as illumination light, and a pseudo-color image may be generated from the reflected light image and the intrinsic fluorescence image, and used as the special light image.

Light having a wavelength band of 790 to 820 nm and light having a wavelength band of 905 to 970 nm (infrared light) may be used as illumination light after intravenously injecting indocyanine green (ICG), and a pseudo-color image may be generated from the reflected light images, and used as the special light image (e.g., infrared imaging (IRI)).

In this embodiment, each section of the image processing section 300 is implemented by hardware. Note that a CPU may perform the process of each section on an image acquired in advance in the same manner as in the first embodiment. Specifically, the process of each section may be implemented by software by causing the CPU to execute a program. Alternatively, part of the process of each section may be implemented by software.

In this embodiment, the special light image may be an in vivo image. The specific wavelength band included in the in vivo image may be the wavelength band of fluorescence emitted from a fluorescent substance. Specifically, the specific wavelength band may be a wavelength band of 490 to 625 nm.

This enables autofluorescence imaging (AFI). Intrinsic fluorescence from a fluorescent substance (e.g., collagen) can be observed by applying excitation light (390 to 470 nm). In this case, the lesion area can be highlighted in a color differing from that of a normal mucous membrane, so that the lesion area can be reliably detected, for example. A wavelength band of 490 to 625 nm is the wavelength band of fluorescence emitted from a fluorescent substance (e.g., collagen) when excitation light is applied. Note that the wavelength band is not limited thereto. For example, the lower limit of the wavelength band may decrease by about 0 to 10%, and the upper limit of the wavelength band may increase by about 0 to 10% depending on a variation factor (e.g., experimental results for the wavelength band of fluorescence emitted from a fluorescent substance). A pseudo-color image may be generated by applying light having a wavelength band of 540 to 560 nm that is absorbed by hemoglobin.

The special light image may be an in vivo image. The specific wavelength band included in the in vivo image may be the wavelength band of infrared light. Specifically, the specific wavelength band may be a wavelength band of 790 to 820 nm or 905 to 970 nm.

This enables infrared imaging (IRI). Information about a blood vessel or the blood flow in a deep area of the mucous membrane that cannot be easily observed visually can be highlighted by intravenously injecting indocyanine green (ICG) (infrared marker) that easily absorbs infrared light, and applying infrared light within the above wavelength band, so that the depth of cancer invasion or the therapeutic strategy can be determined, for example. An infrared marker exhibits maximum absorption in a wavelength band of 790 to 820 nm, and exhibits minimum absorption in a wavelength band of 905 to 970 nm. Note that the wavelength band is not limited thereto. For example, the lower limit of the wavelength band may decrease by about 0 to 10%, and the upper limit of the wavelength band may increase by about 0 to 10% depending on a variation factor (e.g., experimental results for absorption by the infrared marker).

The first and second embodiments according to the invention and the modifications thereof have been described above. Note that the invention is not limited to the first and second embodiments and the modifications thereof. Various modifications and variations may be made without departing from the scope of the invention. A plurality of elements of each of the first and second embodiments and the modifications thereof may be appropriately combined. For example, some elements may be omitted from the first and second embodiments and the modifications thereof The elements described in connection with the first and second embodiments and the modifications thereof may be appropriately combined. Specifically, various modifications and applications are possible without materially departing from the novel teachings and advantages of the invention.

What is claimed is:

1. An image processing device comprising:
a special light image acquisition section configured to acquire an image including an object image that includes information in a specific wavelength band as a special light image;
an attention area detection section configured to detect a lesion area as an attention area on the special light image based on a feature quantity of each pixel of the special light image;
a disappearance determination section configured to determine that the detected attention area has disappeared when the detected attention area is positioned outside the image acquisition range of the special light image;
a guide information generation section configured to generate guide information about the attention area that has disappeared based on a determination result of the disappearance determination section; and
an output control section configured to control output of information including the guide information generated by the guide information generation section.

2. The image processing device as defined in claim 1,
the guide information generation section configured to generate direction information as the guide information, the direction information indicating a direction from an in vivo site corresponding to a display target area to an in vivo site corresponding to the attention area that has disappeared, the display target area being an area displayed on an output section.

3. The image processing device as defined in claim 2,
the guide information generation section configured to generate distance information as the guide information, the distance information indicating a distance from an in vivo site corresponding to the display target area to an in vivo site corresponding to the attention area that has disappeared.

4. The image processing device as defined in claim 1,
the special light image acquisition section configured to acquire a first special light image, a second special light image, and a third special light image;
the attention area detection section configured to detect the attention area within each of the first special light image, the second special light image, and the third special light image acquired by the special light image acquisition section;
the disappearance determination section configured to determine that the attention area has disappeared based on a detection result for the attention area within each of the first special light image, the second special light image, and the third special light image; and
the guide information generation section configured to generate the guide information based on a position of the attention area within the first special light image and a position of the attention area within the second special light image when the disappearance determination section has determined that the attention area has disappeared from the third special light image, and the attention area has not disappeared from the first special light image and the second special light image.

5. The image processing device as defined in claim 4,
the guide information generation section configured to generate the guide information based on a difference between the position of the attention area within the first special light image and the position of the attention area within the second special light image.

6. The image processing device as defined in claim 5,
the guide information generation section configured to calculate a center-of-gravity position of the attention area within the first special light image as the position of the attention area within the first special light image, configured to calculate a center-of-gravity position of the attention area within the second special light image as the position of the attention area within the second special light image, and configured to generate the guide information based on a difference between the position of the attention area within the first special light image and the position of the attention area within the second special light image.

7. The image processing device as defined in claim 5,
the guide information generation section configured to calculate a motion vector of the attention area based on a difference between the position of the attention area within the first special light image and the position of the attention area within the second special light image, and configured to generate the guide information based on the calculated motion vector.

8. The image processing device as defined in claim 7,
the output control section configured to control an output time of the guide information based on the calculated motion vector.

9. The image processing device as defined in claim 8,
the output control section configured to decrease the output time of the guide information when the magnitude of the motion vector is large, and configured to increase the output time of the guide information when the magnitude of the motion vector is small.

10. The image processing device as defined in claim 7,
the guide information generation section including a disappearance direction determination section configured to link the motion vector to one of first direction information to Nth (N is an integer equal to or larger than 2) direction information based on each coordinate component of the motion vector,
the guide information generation section configured to generate one of the first direction information to the Nth direction information that has been linked to the motion vector as the guide information.

11. The image processing device as defined in claim 1,
the special light image acquisition section configured to acquire a plurality of special light images respectively at a plurality of timings;
the attention area detection section configured to detect the attention area within each of the plurality of special light images;
the disappearance determination section determining whether or not configured to determine that the attention area has disappeared based on a detection result for the attention area within each of the plurality of special light images; and
the guide information generation section configured to generate the guide information when the disappearance determination section has determined that the attention area has disappeared from a special light image among the plurality of special light images that has been acquired at an mth (m is an integer equal to or larger than 3) timing among the plurality of timings, and the attention area has not disappeared from at least two special light images among the plurality of special light images that have been acquired at timings among the plurality of timings that precede the mth timing.

12. The image processing device as defined in claim 1,
the special light image acquisition section configured to acquire a plurality of special light images respectively at a plurality of timings;
the attention area detection section configured to detect the attention area within each of the plurality of special light images;
the disappearance determination section configured to determine that the attention area has disappeared based on a detection result for the attention area within each of the plurality of special light images; and
the guide information generation section not generating the guide information when the disappearance determination section has determined that the attention area has disappeared from a special light image among the plurality of special light images that has been acquired at an mth (m is an integer equal to or larger than 3) timing among the plurality of timings, and the attention area has been detected within only one special light image among the plurality of special light images or the attention area has not been detected at a timing that precedes the mth timing.

13. The image processing device as defined in claim 1,
the output control section configured to control an output state of the guide information based on a determination result of the disappearance determination section.

14. The image processing device as defined in claim 13,
the special light image acquisition section configured to acquire a plurality of special light images respectively at a plurality of timings;
the attention area detection section configured to detect the attention area within each of the plurality of special light images;
the disappearance determination section configured to determine that the attention area has disappeared based on a detection result for the attention area within each of the plurality of special light images; and
the output control section configured to continuously output the guide information generated at an Nth (N is an integer equal to or larger than 3) timing from the Nth timing to an (N+K)th (K is an integer equal to or larger than 1) timing when it has been determined that the guide information has started to be output at the Nth timing, and the attention area has continuously disappeared from the Nth timing to the (N+K)th timing.

15. The image processing device as defined in claim 14,
the output control section configured to stop output of the guide information when the attention area has been detected at a timing between the (N+1)th timing and the (N+K)th timing.

16. The image processing device as defined in claim 14,
the output control section configured to stop output of the guide information generated at the Nth timing at an (N+K+1)th timing regardless of whether or not the attention area has disappeared.

17. The image processing device as defined in claim 14,
the output control section including a remaining output time setting section configured to set remaining output time information corresponding to an output time in which the guide information generated at the Nth timing is continuously output from the (N+1)th timing to the (N+K)th timing, the remaining output time setting section setting K as information for setting the remaining output time information.

18. The image processing device as defined in claim 13,
the special light image acquisition section configured to acquire a plurality of special light images respectively at a plurality of timings;
the attention area detection section configured to detect the attention area within each of the plurality of special light images;
the disappearance determination section configured to determine that the attention area has disappeared based on a detection result for the attention area within each of the plurality of special light images; and the output control section configured to continuously present previously generated guide information at consecutive timings when the disappearance determination section has determined that the attention area has continuously disappeared at the consecutive timings.

19. The image processing device as defined in claim 1, further comprising:
an attention level calculation section configured to calculate attention level information that indicates an attention level of the attention area detected within the special light image,
the output control section configured to control an output state of the guide information based on the attention level information calculated by the attention level calculation section.

20. The image processing device as defined in claim 19, the output control section configured to preferentially output the guide information about the attention area determined to have a high attention level as compared with other attention areas based on the attention level information calculated by the attention level calculation section.

21. The image processing device as defined in claim 19, the attention level information including at least one of the feature quantity and reliability of each pixel of the special light image.

22. The image processing device as defined in claim 1, the output control section including an upper limit setting section configured to set an upper limit of a number of pieces of the guide information to be output,
the output control section configured to control an output state of the guide information based on a result of comparison between the number of pieces of the generated guide information and the upper limit set by the upper limit setting section.

23. The image processing device as defined in claim 22, the output control section configured to not output the guide information when the number of pieces of the generated guide information has exceeded the upper limit.

24. The image processing device as defined in claim 1, further comprising:
a normal light image acquisition section configured to acquire an image including an object image that includes information in a wavelength band of white light as a normal light image.

25. The image processing device as defined in claim 24, the output control section configured to output the generated guide information so that the guide information is linked to the normal light image acquired by the normal light image acquisition section.

26. The image processing device as defined in claim 1, further comprising:
an output section configured to output the generated guide information in an output state controlled by the output control section.

27. The image processing device as defined in claim 1, the specific wavelength band being narrower than a wavelength band of white light.

28. The image processing device as defined in claim 27, the special light image being an in vivo image; and
the specific wavelength band included in the in vivo image being a wavelength band of a wavelength absorbed by hemoglobin in blood.

29. The image processing device as defined in claim 28, the specific wavelength band being 390 to 445 nm or 530 to 550 nm.

30. The image processing device as defined in claim 1, the special light image being an in vivo image; and
the specific wavelength band included in the in vivo image being a wavelength band of fluorescence emitted from a fluorescent substance.

31. The image processing device as defined in claim 30, the specific wavelength band being 490 to 625 nm.

32. The image processing device as defined in claim 1, the special light image being an in vivo image; and
the specific wavelength band included in the in vivo image being a wavelength band of infrared light.

33. The image processing device as defined in claim 32, the specific wavelength band being 790 to 820 nm or 905 to 970 nm.

34. An information storage device having stored thereon a program, the program causing a computer to function as:
a special light image acquisition section configured to acquire an image including an object image that includes information in a specific wavelength band as a special light image;
an attention area detection section configured to detect a lesion area as an attention area on the special light image based on a feature quantity of each pixel of the special light image;
a disappearance determination section configured to detect that the detected attention area has disappeared when the detected attention area is positioned outside the image acquisition range of the special light image;
a guide information generation section configured to generate guide information about the attention area that has disappeared based on a determination result of the disappearance determination section; and
an output control section configured to control output of information including the guide information generated by the guide information generation section.

* * * * *